United States Patent
Prien et al.

(10) Patent No.: US 7,598,263 B2
(45) Date of Patent: Oct. 6, 2009

(54) CYANOQUINOLINE DERIVATIVES, THEIR PREPARATION, THEIR USE, AND MEDICAMENTS COMPRISING THEM

(75) Inventors: Olaf Prien, Berlin (DE); Knut Eis, Berlin (DE); Wolfgang Schwede, Glienicke (DE); Judith Guenther, Berlin (DE); Dieter Zopf, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 11/765,813

(22) Filed: Jun. 20, 2007

(65) Prior Publication Data

US 2008/0108627 A1    May 8, 2008

Related U.S. Application Data

(60) Provisional application No. 60/816,628, filed on Jun. 27, 2006.

(30) Foreign Application Priority Data

Jun. 21, 2006 (DE) ........................ 10 2006 029 445

(51) Int. Cl.
  A61K 31/435 (2006.01)
  C07D 215/00 (2006.01)
(52) U.S. Cl. ........................................ 514/291; 546/80
(58) Field of Classification Search ............ 546/80; 514/291
  See application file for complete search history.

(56) References Cited

U.S. PATENT DOCUMENTS 5,506,235 A    4/1996    Moyer et al.

FOREIGN PATENT DOCUMENTS

EP    0 081 836 A1    6/1983
WO    WO 93/03030 A1    2/1993

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
G. Rewcastle et al., "Tyrosine Kinase Inhibitors. 9. Synthesis and Evaluation of Fused Tricyclic Quinazoline Analogues as ATP Site Inhibitors of the Tyrosine Kinase Activity of the Epidermal Growth Factor Receptor", J. Med. Chem., vol. 39 (1996) pp. 918-928.
M.G. Ferlin et al., "Synthesis and Antiproliferative Activity of Some New DNA-Targeted Alkylating Pyrroloquinolines", Bioorganic & Medicinal Chemistry, vol. 12 (2004) pp. 771-777.
V. Milata et al., "Thermal Cyclocondensations of 3-N(4- and 5-Benzimidazolyl and Benztriazolyl)Amino Derivatives of 2-Propenoic Acid", Collection Czechoslovak Chem. Commun., vol. 52 (1987) pp. 2918-2925.

* cited by examiner

*Primary Examiner*—Kamal A Saeed
*Assistant Examiner*—Samantha L Shterengarts
(74) *Attorney, Agent, or Firm*—Millen, White, Zelano & Branigan, P.C.

(57) ABSTRACT

The present invention relates to a quinoline derivative having the general formula (A):

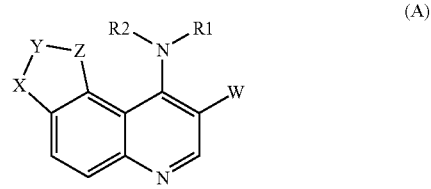

in which $R^1$, $R^2$, X, Y and Z are indicated in the description and the claims, the use of the compounds of the general formula (A) for the treatment of various disorders, and the preparation of compounds of the general formula (A).

17 Claims, No Drawings

CYANOQUINOLINE DERIVATIVES, THEIR PREPARATION, THEIR USE, AND MEDICAMENTS COMPRISING THEM

This application claims the benefit of the filing date of U.S. Provisional Application Ser. No. 60/816,628, filed Jun. 27, 2006, which is incorporated by reference herein.

SUMMARY OF THE INVENTION

The invention relates to certain quinoline derivatives, their preparation and use as inhibitor of protein kinases, in particular of Eph (erythropoietin-producing hepatoma amplified sequence) receptors for the treatment of various disorders.

Protein tyrosine kinases catalyze the phosphorylation of specific tyrosine residues in various proteins. Such phosphorylation reactions play a part in a large number of cellular processes which are involved in the regulation of growth and differentiation of cells. Protein tyrosine kinases are divided into receptor and non-receptor tyrosine kinases. The family of receptor tyrosine kinases (RTKs) consists of 58 kinases (Manning G. et al. 2002, *Science* 298, 1912-1934). RTKs have an extracellular ligand binding domain, a transmembrane domain and an intracellular domain which usually comprises the tyrosine kinase activity. RTKs mediate signal transduction from extracellular stimulators such as, for example, growth factors. The ligand binding leads to dimerization of the RTKs and reciprocal autophosphorylation of their intracellular domains. Depending on the cell type, specific intracellular binding proteins are recruited thereby (inter alia non-receptor tyrosine kinases), via which signal processing takes place in the cell (Schlessinger J. 2000, *Cell* 103, 211-225). These include receptor families of growth factors such as EGF (epidermal growth factor), VEGF (vascular endothelial growth factor), FGF (fibroblast growth factor), PDGF (platelet derived growth factor) and NGF (nerve growth factor), and of the insulin receptors, and the large family of ephrin receptors and others.

The ephrin (Eph) receptors constitute the largest family within the RTKs. They are divided according to their sequential relationship and their ligand specificity into the group of EphA receptors (9 members) and of EphB receptors (6 members) (Kullander K. and Klein R. 2002, *Nat. Rev. Mol. Cell Biol.* 3, 475-486; Cheng N. et al. 2002, Cyt. and growth factor Rev. 13, 75-85). Eph receptors are activated by membrane-associated ligands of the EphrinA or EphrinB family. EphrinAs are anchored in the cell membrane via glycolipids (GPI), whereas EphrinBs have a transmembrane region and an intracellular domain. The interaction between Ephrins and the Eph receptors leads to a bidirectional signal transmission in the ephrin-expressing and in the Eph-receptor-carrying cells. Ephrins and Eph receptors play a part in a large number of morphogenetic processes in embryonic development and in the adult organism. They are involved in embryo patterning, in the development of the blood vessel system (Gerety S. S: et al 1999, *Mol. Cell.* 4, 403-414) and in the establishment of neuronal interconnections (Flanagan, J. G. and Vanderhaeghen, P., 1998, *Annu. Rev. Neurosci.* 21, 309-345). In the adult organism, they are involved in neovascularization processes, e.g. in tumour development and in endometriosis, and in the morphogenesis of the intestinal epithelium (Batlle E. et al. 2002, *Cell* 111:251-63). At the cellular level, they mediate migration, adhesion and juxtacrine cell contacts. Elevated expression of Eph receptors such as, for example, EphB2 and EphB4 has also been observed in various tumour tissues such as, for example, breast and bowel tumours (Nakamoto M. and Bergemann A. D. 2002, *Mic. Res. Tech.* 59, 58-67). EphB2, EphB3 and EphB4 knockout mice show defects in the formation of the blood vessel system. The embryonic lethality of EphB4–/– mice in embryonic stage d14 shows the special role of EphB4 in this process (Gerety S. S: et al 1999, *Mol. Cell.* 4, 403-414). Modulation of these receptors, e.g. by inhibiting their kinase activity, leads for example to suppression of tumour growth and/or tumour metastasis either through a direct antitumour or through an indirect antiangiogenic effect.

Non-receptor tyrosine kinases occur in soluble form inside cells and are involved in the processing of extracellular signals (e.g. from growth factors, cytokines, antibodies, adhesion molecules) inside the cell. They include inter alia the families of src (sarcoma) kinases, of Tec (tyrosine kinase expressed in hepatocellular carcinoma) kinases, of Abl (Abelson) kinases and of Brk (breast tumor kinase) kinases, and the focal adhesion kinase (FAK).

An altered activity of these protein tyrosine kinases may lead to a wide variety of physiological disorders in the human body and thus cause for example inflammatory, neurological and oncological disorders.

WO 01/19828 A discloses a wide variety of kinase inhibitors.

US 2004116388 A discloses triazine compounds which inhibit receptor tyrosine kinases.

WO 03/089434 A discloses imidazo[1,2a]pyrazin-8-ylamines, and WO 04/00820 A discloses various aromatic monocycles, which inhibit receptor tyrosine kinases.

EP 0 187 705 A2 describes imidazo[4,5f]quinolines which exhibit an immunomodulating effect in infectious diseases. Likewise, U.S. Pat. No. 5,506,235 A describes imidazo[4,5f] quinolines with an immunostimulating effect.

WO 04/006846 A discloses various quinazoline derivatives which inhibit receptor tyrosine kinases.

WO 03/053960 describes substituted 3-cyanoquinoline derivatives as MEK inhibitors.

US2005/0026933 claims quinolinecarbonitriles as EGFR inhibitors.

WO 01/68186 describes cyanoquinolines for the treatment of intestinal polyps.

However, no Eph receptor inhibitors are described among the receptor tyrosine kinase inhibitors.

It is an object of the present invention to provide compounds which inhibit receptor tyrosine kinases, especially Eph receptors.

The object is achieved by quinoline derivatives having the general formula (A), a process for preparing the quinoline derivative, the uses of the quinoline derivative, and a medicament comprising the quinoline derivative, according to the following description and the claims.

The present invention relates to a quinoline derivative having the general formula (A):

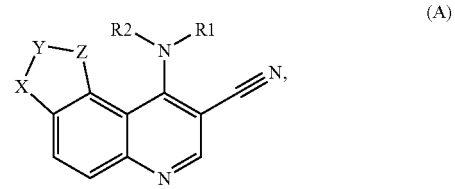

(A)

where
$R^1$ and $R^2$ are identical or different and are selected independently of one another from the group comprising hydrogen, hydroxy, halogen, nitro, cyano, —$C_1$-$C_6$-alkyl, —$C_1$-$C_4$- hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p PO_3(R^6)_2$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$, or —$OR^5$, where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally form together a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

X, Y, Z are identical or different and are selected independently of one another from the group comprising —$CR^3$=, —$CR^3R^4$—, —C(O)—, —N=, —S—, —O—, —$NR^3$—, —$S(O)_2$—, —S(O)— and —$S(O)(N=R^3)$—, and single or double bonds are present between X, Y and Z, but a maximum of one of the three radicals X, Y and Z is identical with —O—, furthermore at most one of the three radicals X, Y and Z is identical with —N= or —$NR^3$—;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl is unsubstituted or substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or $NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

m', m"=independently of one another 0, 1, 2, 3, or 4, n=1, 2, 3, 4, 5, or 6, p=0, 1, 2, 3, 4, 5, or 6, and the N-oxides, solvates, hydrates, stereoisomers, diastereomers, enantiomers and salts thereof.

A preferred subgroup are compounds in which:

$R^1$ and $R^2$ are identical or different and are selected independently of one another from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$ where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

X, Y, Z are identical or different and are selected independently of one another from the group comprising —$CR^3$=, —$CR^3R^4$—, —C(O)—, —N=, —S—, —O—, —$NR^3$—, —$S(O)_2$—, —S(O)— and —$S(O)(N=R^3)$—, and single or double bonds are present between X, Y and Z, but a maximum of one of the three radicals X, Y and Z is identical with —O—, furthermore at most one of the three radicals X, Y and Z is identical with —N= or —$NR^3$—;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-

$C_{12}$-heterocycloalkyl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl is unsubstituted or is substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or $NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

m', m"=independently of one another 0, 1, 2, 3, or 4, n=1, 2, 3, 4, 5, or 6, p=0, 1, 2, 3, 4, 5, or 6, and the N-oxides, solvates, hydrates, stereoisomers, diastereomers, enantiomers and salts thereof.

More preference is given to compounds of the general formulae (A1) to (A5):

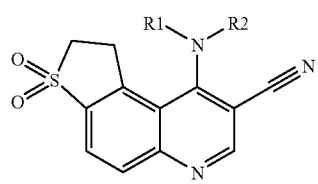

(A1)

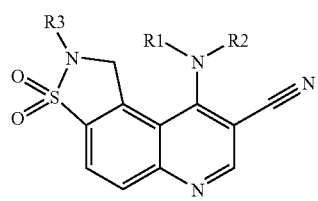

(A2)

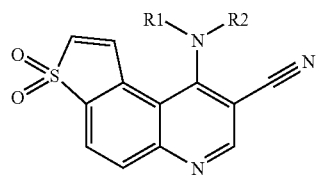

(A3)

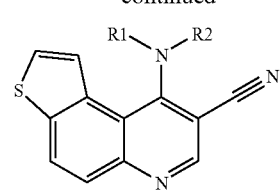

(A4)

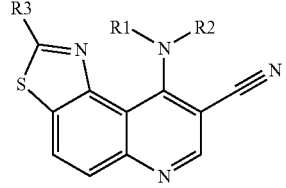

(A5)

where:

$R^1$ and $R^2$ are identical or different and are selected independently of one another from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$ where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

$R^3$ and $R^4$ are selected independently of one another from the group comprising hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl is unsubstituted or is substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ optionally together form a bridge of 3-10 methylene units, where up to two methylene units are optionally replaced by O, S or $NR^4$;

$R^7$, $R^8$ are identical or different and are selected independently of one another from the group comprising hydrogen, —$C_1$-$C_4$-alkyl, —$C_6$-$C_{12}$-aryl and —$C_5$-$C_{18}$-heteroaryl, where alkyl, aryl, heteroaryl is unsubstituted or is substituted one or more times independently of one another by halogen or alkoxy, or $R^7$ and $R^8$ optionally together form a bridge of 3-10 methylene units, where up to two methylene units are optionally replaced by O, S or —$NR^4$;

m', m"=independently of one another 0, 1, 2, 3, or 4, n=1, 2, 3, 4, 5, or 6, p=0, 1, 2, 3, 4, 5, or 6, and the N-oxides, solvates, hydrates, stereoisomers, diastereomers, enantiomers and salts thereof.

Particular preference is given to compounds of the general formulae:

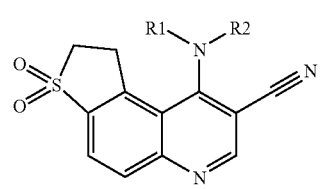

(A1)

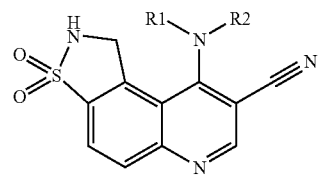

(A2)

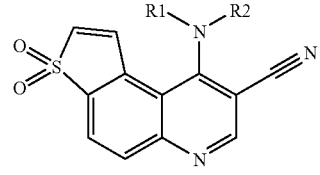

(A3)

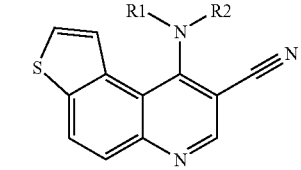

(A4)

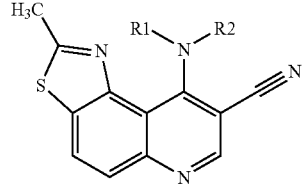

(A5)

where:

$R^1$ and $R^2$ are identical or different and are selected independently of one another from the group comprising hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$ and —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl or —$C_1$-$C_6$-alkoxy are unsubstituted or are substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$ where the carbon framework of the —$C_3$-$C_{10}$-cycloalkyl and of the —$C_1$-$C_{10}$-alkyl may comprise one or more times independently of one another nitrogen, oxygen, sulphur atoms, —$NR^4$ or C=O groups or one or more double bonds, or $R^1$ and $R^2$ optionally together form a bridge of 3-10 methylene units, where up to two methylene units are optionally replaced by O, S or —$NR^4$, and where the phenyl radical is optionally substituted one or more times independently of one another by hydroxy, halogen, nitro, cyano, phenyl, —$NR^5R^6$, alkyl or —$OR^5$;

$R^4$ is hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl or —$C_1$-$C_{10}$-alkanoyl is unsubstituted or is substituted one or more times independently of one another by hydroxy, halogen, nitro, cyano, phenyl, —$NR^5R^6$, alkyl, —$SR^5$ or —$OR^5$, $R^5$ and $R^6$ are identical or different and are selected independently of one another from the group comprising hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl or —$C_5$-$C_{18}$-heteroaryl are unsubstituted or are substituted one or more times independently of one another by hydroxy, halogen, cyano, nitro, —OR$^7$, —NR$^7$R$^8$, —C(O)NR$^7$R$^8$, —C(O)OR$^7$ or —C$_1$-C$_6$-alkyl, where —C$_1$-C$_6$-alkyl is unsubstituted or is substituted one or more times independently of one another by halogen, hydroxy, cyano, —NR$^7$R$^8$, —OR$^7$ or phenyl; or R$^5$ and R$^6$ optionally together form a bridge of 3-10 methylene units, where up to two methylene units are optionally replaced by O, S or NR$^4$;

R$^7$, R$^8$ are identical or different and are selected independently of one another from the group comprising hydrogen, —C$_1$-C$_4$-alkyl, —C$_6$-C$_{12}$-aryl and —C$_5$-C$_{18}$-heteroaryl, where alkyl, aryl, heteroaryl is unsubstituted or is substituted one or more times independently of one another by halogen or alkoxy, or R$^7$ and R$^8$ optionally together form a bridge of 3-10 methylene units, where up to two methylene units are optionally replaced by O, S or —NR$^4$;

m', m"=independently of one another 0, 1, 2, 3, or 4, n=1, 2, 3, 4, 5, or 6, p=0, 1, 2, 3, 4, 5, or 6, and the N-oxides, solvates, hydrates, stereoisomers, diastereomers, enantiomers and salts thereof.

The following compounds are preferred:

9-[(3-hydroxy-5-methoxyphenyl)amino]-1,2-dihydrothieno[3,2-f]quinoline-8-carbonitrile 3,3-dioxide;

9-[(3-methoxyphenyl)amino]-1,2-dihydrothieno[3,2-f]quinoline-8-carbonitrile 3,3-dioxide;

9-[(3-hydroxy-4-methylphenyl)amino]-1,2-dihydrothieno[3,2-f]quinoline-8-carbonitrile 3,3-dioxide;

1-{3-[(8-cyano-3,3-dioxido-1,2-dihydrothieno[3,2-f]quinolin-9-yl)amino]phenyl}-3-[3-(trifluoromethyl)phenyl]urea; and 9-[(3-methoxyphenyl)amino]thieno[2,3-f]quinoline-8-carbonitrile.

It has been found that the compounds according to the invention are able to inhibit receptor tyrosine kinases, especially Eph receptors.

Alkyl means in each case a straight-chain or branched alkyl radical such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy means in each case a straight-chain or branched alkoxy radical such as, for example, methoxy, ethoxy, propoxy, isopropoxy, butoxy, isobutoxy, sec butoxy, pentyloxy, isopentyloxy, hexyloxy, heptyloxy, octyloxy, nonyloxy or decyloxy.

The alkenyl substituents are in each case straight-chain or branched, with the following radicals being meant for example: vinyl, prop-1-enyl, prop-2-enyl, but-1-enyl, 1-ethylethenyl, but-2-enyl, 1-methylprop-1-enyl, 2-methylprop-2-enyl, 2-methylprop-1-enyl, 1-methylprop-2-enyl, but-3-enyl.

Alkynyl means in each case a straight-chain or branched alkynyl radical which comprises two to six, preferably two to four, C atoms. Examples of suitable radicals are the following: ethynyl, prop-1-ynyl, prop-2-ynyl, but-1-ynyl, but-2-ynyl, but-3-ynyl.

Cycloalkyl means monocyclic alkyl rings such as cyclopropyl, cyclobutyl, cyclopentyl, cyclohexyl or cycloheptyl, but also bicyclic rings or tricyclic rings such as, for example, adamantanyl. The cycloalkyl rings may be unsubstituted or substituted one or more times. Cycloalkyls according to this invention comprise C$_3$-C$_{12}$ carbon atoms; cycloalkyls having C$_3$-C$_{10}$ carbon atoms are preferred, and cycloalkyls having C$_3$-C$_6$ carbon atoms are particularly preferred.

An aryl radical has 6-12 carbon atoms in each case. The radical may be mono- or bicyclic, for example naphthyl, biphenyl and, in particular, phenyl.

The heteroaryl radical includes an aromatic ring system which comprises in each case 5-18 ring atoms, preferably 5 to 10 ring atoms and particularly preferably 5 to 7 ring atoms and, instead of the carbon, one or more identical or different heteroatoms from the group of oxygen, nitrogen or sulphur. The radical may be mono-, bi- or tricyclic and additionally in each case benzo-fused. However, only those combinations which are sensible in the view of a skilled person, especially in relation to the ring tension, are meant.

The heteroaryl rings may be unsubstituted or substituted one or more times. Examples which may be mentioned are: thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl and benzo derivatives of these radicals such as, for example, 1,3-benzodioxolyl, benzofuranyl, benzothienyl, benzoxazolyl, benzimidazolyl, indazolyl, indolyl, isoindolyl, oxepinyl, azocinyl, indolizinyl, indolyl, isoindolyl, indazolyl, benzimidazolyl, purinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl etc.

Halogen means in each case fluorine, chlorine, bromine or iodine.

C$_3$-C$_{12}$-Heterocycloalkyl stands for an alkyl ring including 3-12 carbon atoms, preferably including 3 to 10 carbon atoms and particularly preferably including 3 to 6 carbon atoms, which is interrupted by at least one of the following atoms nitrogen, oxygen and/or sulphur in the ring and which may optionally be interrupted by one or more identical or different —(CO)—, —SO— or —SO$_2$— groups in the ring and optionally comprises one or more double bonds in the ring. However, only those combinations which are sensible in the view of a skilled person, especially in relation to the ring tension, are meant. C$_3$-C$_{12}$-Heterocycloalkyls according to this invention are monocyclic, but also bicyclic or tricyclic. Examples of monocyclic heterocyclyles which may be mentioned are: oxiranyl, oxetanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl etc.

As used in this application, "C$_1$-C$_{10}$" refers, for example in connection with the definition of "C$_1$-C$_{10}$-alkyl", to an alkyl group having a finite number of 1 to 10 carbon atoms, i.e. 1, 2, 3, 4, 5, 6, 7, 8, 9 or 10 carbon atoms. The definition of "C$_1$-C$_{10}$" is further interpreted to mean that every possible sub-range such as, for example, C$_1$-C$_{10}$, C$_2$-C$_9$, C$_3$-C$_8$, C$_4$-C$_7$, C$_5$-C$_6$, C$_1$-C$_2$, C$_1$-C$_3$, C$_1$-C$_4$, C$_1$-C$_5$, C$_1$-C$_6$, C$_1$-C$_7$, C$_1$-C$_8$, C$_1$-C$_9$, C$_1$-C$_{10}$, preferably C$_1$-C$_2$, C$_1$-C$_3$, C$_1$-C$_4$, C$_1$-C$_5$, C$_1$-C$_6$; preferably C$_1$-C$_4$ is also included in the definition.

In analogy thereto "C$_2$-C$_{10}$" refers, for example in connection with the definition of "C$_2$-C$_{10}$-alkenyl" and "C$_2$-C$_{10}$-alkynyl", to an alkenyl group or alkynyl group having a finite number of 2 to 10 carbon atoms, i.e. 2, 3, 4, 5, 6, 7, 8, 9 or 10 carbon atoms. The definition of "C$_2$-C$_{10}$" is interpreted to mean that every possible sub-range such as, for example, C$_2$-C$_{10}$, C$_3$-C$_9$, C$_4$-C$_8$, C$_5$-C$_7$, C$_2$-C$_3$, C$_2$-C$_4$, C$_2$-C$_5$, C$_2$-C$_6$, C$_2$-C$_7$, C$_2$-C$_8$, C$_2$-C$_9$, preferably C$_2$-C$_4$, is also included in the definition.

Furthermore, "C$_1$-C$_6$" refers, for example in connection with the definition of "C$_1$-C$_6$-alkoxy" to an alkoxy group having a finite number of 1 to 6 carbon atoms, i.e. 1, 2, 3, 4, 5 or 6 carbon atoms. The definition of "C$_1$-C$_6$" is interpreted to mean that every possible sub-range such as, for example, $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_4$, is also included in the definition.

All statements of ranges in the application which are not explicitly mentioned here are defined analogously like the ranges "$C_1$-$C_{10}$", "$C_2$-$C_{10}$" and "$C_1$-$C_6$" mentioned above as examples.

The term "one or more times", e.g. in the definition of the substituents of the compounds of the general formulae of the present invention, is understood as meaning "one, two, three, four or five times, particularly one, two, three or four tines, more particularly one, two or three times, more particularly one or two times".

Isomers mean chemical compounds of the same molecular formula but different chemical structure. A distinction is made in general between constitutional isomers and stereoisomers. Constitutional isomers have the same molecular formula but differ through the mode of linkage of their atoms or atomic groups. Included herein are functional isomers, positional isomers, tautomers or valence isomers. Stereoisomers have fundamentally the same structure (constitution) and thus also the same molecular formula, but differ through the spatial arrangement of the atoms. In general, configurational isomers and conformational isomers are distinguished. Configurational isomers are stereoisomers which can be interconverted only by breaking bonds. These include enantiomers, diastereomers and E/Z (cis/trans) isomers. Enantiomers are stereoisomers which are related to one another as image and mirror image and have no plane of symmetry. All stereoisomers which are not enantiomers are referred to as diastereomers. E/Z (cis/trans) isomers at double bonds are a special case. Conformational isomers are stereoisomers which can be interconverted by rotation of single bonds. To distinguish the types of isomerism from one another, see also the IUPAC rules section E (*Pure Appl. Chem.* 1976, 45, 11-30).

The quinoline derivatives according to the invention having the general formula A also encompass the possible tautomeric forms and include the E or Z isomers or, if a chiral centre is present, also the racemates and enantiomers. By these are also meant double-bond isomers.

The quinoline derivatives according to the invention may also exist in the form of solvates, in particular of hydrates, in which case the compounds according to the invention accordingly comprise polar solvents, in particular water, as structural element of the crystal lattice of the compounds according to the invention. The proportion of polar solvent, in particular water, may be in a stoichiometric or else non-stoichiometric ratio. Terms used in connection with stoichiometric solvates, hydrates are also hemi-, (semi-), mono-, sesqui-, di-, tri-, tetra-, penta-, etc. solvates or hydrates.

N-Oxides means that at least one nitrogen of the compounds according to the invention of the general formula (A) may be oxidized.

If an acidic function is present, suitable salts are the physiologically tolerated salts of organic and inorganic bases such as, for example, the readily soluble alkali metal and alkaline earth metal salts, and salts of N-methylglucamine, dimethylglucamine, ethylglucamine, lysine, 1,6-hexanediamine, ethanolamine, glucosamine, sarcosine, serinol, trishydroxymethylamino-methane, aminopropanediol, Sovak base, 1-amino-2,3,4-butanetriol.

If a basic function is present, the physiologically tolerated salts of organic and inorganic acids are suitable, such as hydrochloric acid, hydrobromic acid, sulphuric acid, phosphoric acid, oxalic acid, malonic acid, maleic acid, citric acid, succinic acid, tartaric acid and others.

Functional groups may be protected where appropriate by protective groups during the reaction sequence. Such protective groups may be inter alia esters, amides, ketals/acetals, nitro groups, carbamates, alkyl ethers, allyl ethers, benzyl ethers or silyl ethers. Compounds which may occur as constituent of silyl ethers inter alia are such as, for example, trimethylsilyl (TMS), tert-butyldimethylsilyl (TBDMS), tert-butyldiphenylsilyl (TBDPS), triethylsilyl (TES), etc. The preparation thereof is described in the experimental section.

The quinoline derivatives according to the invention having the general formula A inhibit receptor tyrosine kinases, especially Eph kinases, on which their effect is also based, for example in the treatment of disorders in which angiogenesis, lymphangiogenesis or vasculogenesis are involved, of disorders of the blood vessels, disorders caused by hyperproliferation of body cells, or chronic or acute neurodegenerative disorders. The present quinoline derivatives having the general formula (A) can accordingly be used as medicaments.

Treatments are preferably carried out on humans, but also on related mammalian species such as, for example, dog and cat.

Angiogenic and/or vasculogenic disorders can be treated by the growth of blood vessels being inhibited (antiangiogenic) or promoted (proangiogenic). Antiangiogenic uses take place for example in tumour angiogenesis, endometriosis, in diabetes-related or other retinopathies or in age-related macular degeneration. Proangiogenic uses take place for example in myocardial infarction or acute neurodegenerative disorders due to ischaemias of the brain or neurotraumata.

Blood vessel disorders mean stenoses, arterioscleroses, restenoses or inflammatory diseases such as rheumatoid arthritis.

Hyperproliferative disorders mean solid tumours, non-solid tumours or non-carcinogenic hyperproliferation of cells in the skin, where solid tumours mean inter alia tumours of the breast, colon, kidney, lung and/or brain. Non-solid tumours mean inter alia leukaemias, and non-carcinogenic hyperproliferation of cells in the skin means inter alia psoriasis, eczemas, scleroderma or benign prostatic hypertrophy.

Chronic neurodegenerative disorders mean inter alia Huntington's disease, amyotrophic lateral sclerosis, Parkinson's disease, AIDS-induced dementia or Alzheimer's disease.

The quinoline derivatives having the general formula (A) can likewise be used for diagnostic purposes in vitro or in vivo for identifying receptors in tissues by means of autoradiography and/or PET.

The substances can in particular for diagnostic purposes also be radiolabelled.

For use of the quinoline derivatives according to the invention as medicaments, they are converted into the form of a pharmaceutical product which, besides the active ingredient, comprises pharmaceutical, organic or inorganic inert carrier materials which are suitable for enteral or parenteral administration, such as, for example, water, gelatin, gum arabic, lactose, starch, magnesium stearate, talc, vegetable oils, polyalkylene glycols etc. The pharmaceutical products may be in solid form, for example as tablets, coated tablets, suppositories, capsules or in liquid form, for example as solutions, suspensions or emulsions. They additionally comprise where appropriate excipients such as preservatives, stabilizers, wetting agents or emulsifiers; salts to modify the osmotic pressure or buffers.

The present invention likewise relates to these pharmaceutical products.

Suitable for parenteral use are in particular solutions for injection or suspensions, especially aqueous solutions of the active compounds in polyhydroxyethoxylated castor oil.

Carrier systems which can also be used are surface-active excipients such as salts of bile acids or animal or vegetable phospholipids, but also mixtures thereof, and liposomes or their constituents.

Suitable for oral use are, in particular, tablets, coated tablets or capsules with talc and/or hydrocarbon carriers or binders, such as, for example, lactose, maize starch or potato starch. Use can also take place in liquid form, for example as solution, to which a sweetener is added where appropriate.

The present invention likewise relates to the enteral, parenteral and oral administrations.

The dosage of the active ingredients may vary depending on the route of administration, age and weight of the patient, nature and severity of the disorder to be treated and similar factors. The daily dose is 0.5-1000 mg, it being possible to give the dose as a single dose to be administered once or divided into two or more daily doses.

The present invention likewise relates to medicaments for the treatment of the abovementioned disorders, which comprise at least one quinoline derivative having the general formula (A), where the medicaments may where appropriate comprise suitable formulation substances and carriers.

Where no description is given for the preparation of the starting compounds, they are known to the skilled person or can be prepared in analogy to known compounds or to processes described herein. It is likewise possible to carry out all the reactions described herein in parallel reactors or using combinatorial operating techniques.

The mixtures of isomers can be fractionated by conventional methods such as, for example, crystallization, chromatography or salt formation into the enantiomers or E/Z isomers.

Salts are prepared in a conventional way by mixing a solution of the compound having the general formula (A) with the equivalent amount or an excess of a base or acid, which is in solution where appropriate, and removing the precipitate or working up the solution in a conventional way.

The present invention likewise relates to the process for preparing the quinoline derivatives according to the invention.

The intermediates preferably used for preparing the quinoline derivatives according to the invention having the general formula (A) are the following compounds having the general formulae (I) to (V).

General Description of the Preparation of the Compounds According to the Invention:

Scheme 1

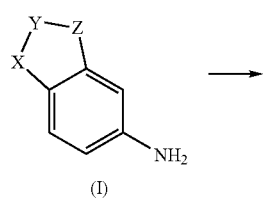

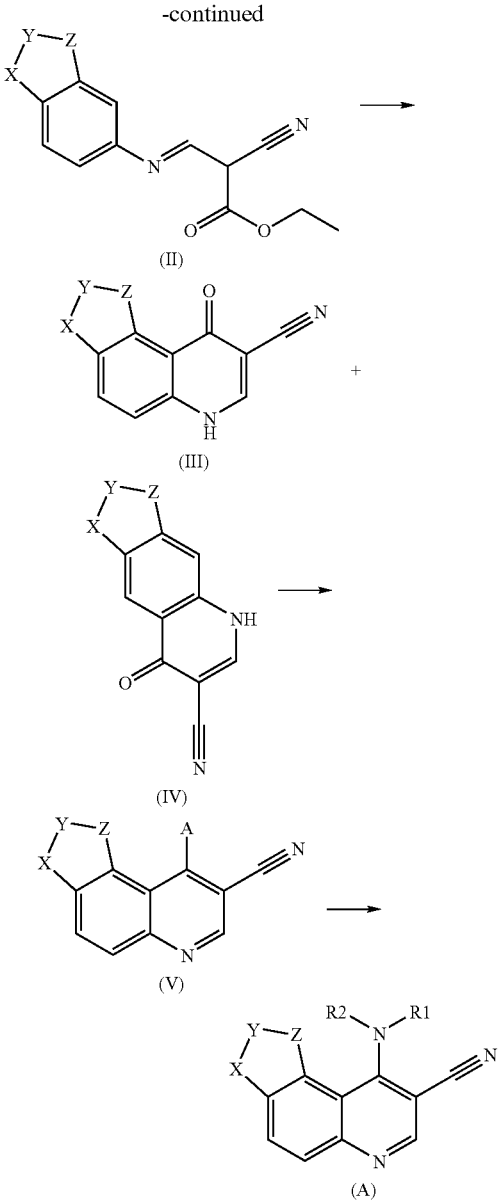

Quinoline derivatives according to the invention having the general formula (A) can be prepared for example by the route shown in scheme 1, in which the radical A can be for example halogen or $-OS(O)_2C_nF_{2n+1}$ with n=1-3 and the radicals R1 and R2 may be as described in the claims, and the radicals X, Y and Z have the same meaning as in the general formula (A). The required starting materials are either commercially available or are prepared by processes disclosed in the literature, or in analogy to processes disclosed in the literature, or as described below.

Addition of ethyl (ethoxymethylene)cyanoacetate onto a compound having the general formula (I) forms compounds having the general formula (II). These compounds are then cyclized, preferably under thermal conditions, to compounds having the general formula (III) (cf. Bioorg. Med. Chem. Lett. 2000, 10, 2815-2828). It is also possible to employ acids or Lewis acids in these cyclizations (cf. *Monatsh. Chemie* 1978, 109, 527). The by-products of the general formula (IV) which may likewise be formed in this case can be removed at this stage.

Compounds having the general formula (V) are then prepared for example by reaction with thionyl chloride or phosphoryl chloride (for A=Cl) or perfluoroalkylsulphonic anhydrides (for A=perfluoroalkylsulphonyl) (cf. *J. Med. Chem.* 2005, 48, 1107-1131.) Compounds having the general formula (A) can then be prepared from compounds of the general formula (V) by addition of amines. Coupling with the amines can take place under acidic, basic or neutral conditions, but also by transition metal-catalyzed coupling in the presence of suitable ligands (cf. *Angew. Chemie* 1998, 110, 2154-2177; *Angew. Chemie* 2000, 112, 4666-4668).

The radicals X, Y and Z can where appropriate be further modified. Functional groups possibly present in the intermediates, such as carbonyl groups, hydroxy groups or amino groups, can be protected in the interim with protective groups by known processes.

An alternative preparation of compounds of the general formula (A) starting from anthranilic acid derivatives is described for example in the literature (*J. Med. Chem.* 2001, 44, 822-833).

It is alternatively possible before the reaction management described previously to prepare the final compounds according to the invention by parallel synthesis, for example in an automatic synthesizer.

Examples of ring systems according to the invention corresponding to the general formula (A) are given below:

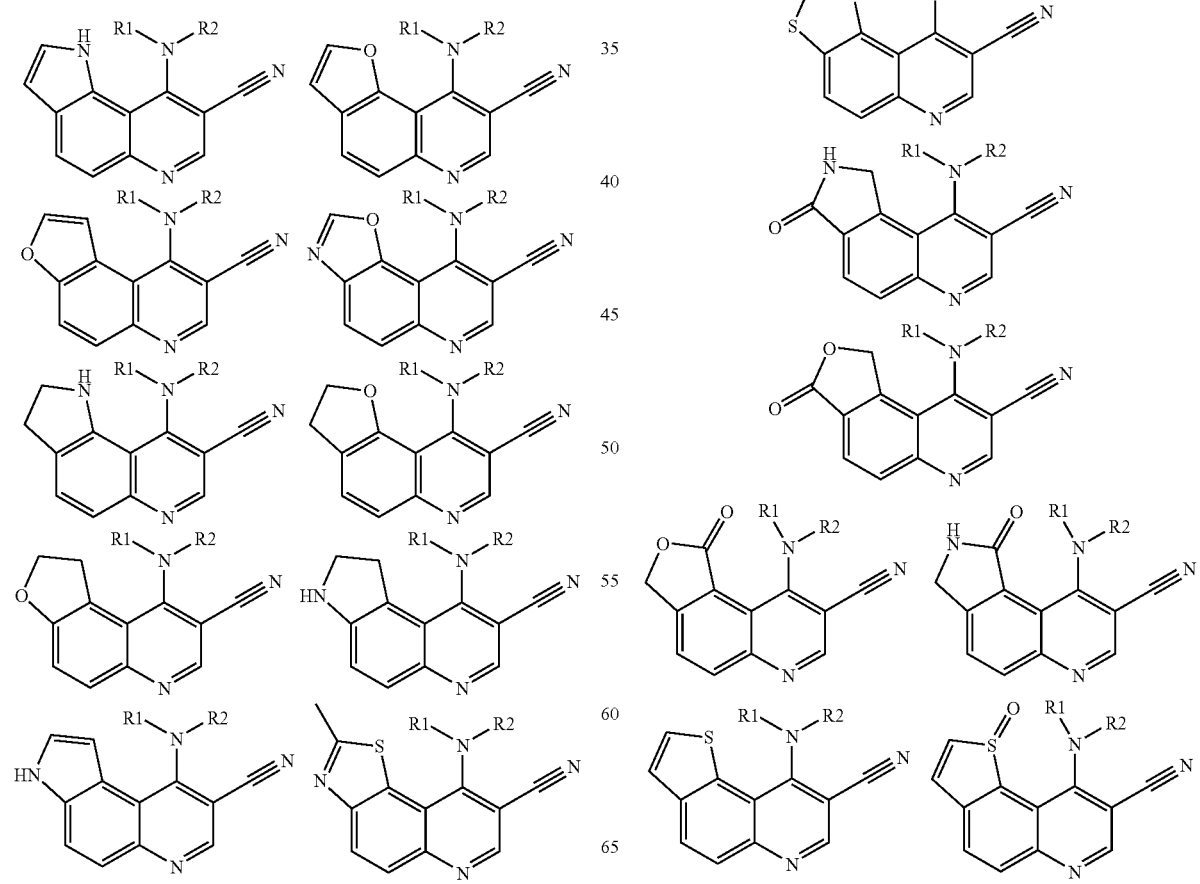

-continued

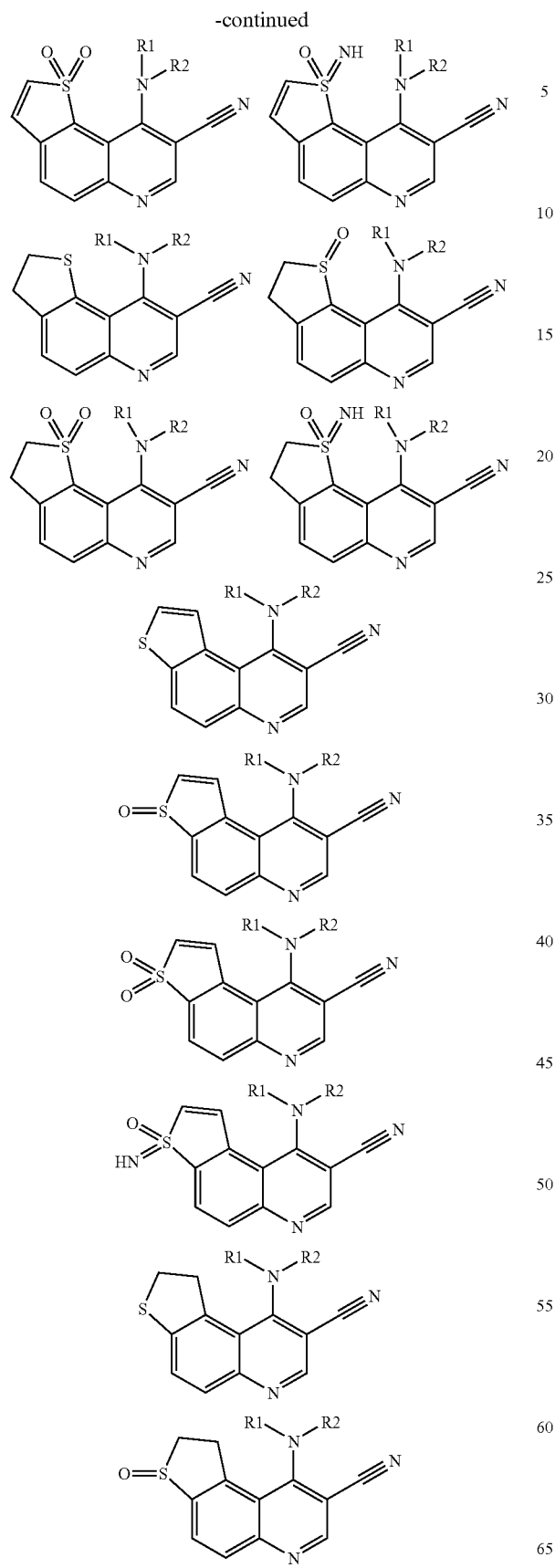

Experimental Description of the Preparation of the Intermediates and of the Products According to the Invention of the General Formula (A).

General Part

LC-MS analyses were carried out using the following methods and instruments:

LC-MS Method A

The separations were carried out on an Acquity HPLC (Waters) coupled to a Micromass/Waters ZQ 4000 mass spectrometer. An X-bridge (Waters) column (dimensions: 2.1×50 mm, packed with 1.7 μm BEH packing material) was employed for the separation. Water/acetonitrile mixtures (each with 0.05% formic acid) were used as mobile phase with a flow rate of 1.3 ml/minute; gradient: 10-90% acetonitrile in 1.7 minutes, 0.2 minutes with 90% acetonitrile, followed by a gradient again to 10% acetonitrile (total running time: 2.5 minutes). UV data (200-400 nm) and mass traces (160-800 Daltons; cone voltage 20 V) were recorded in the stated ranges.

LC-MS Method B

Data were recorded in analogy to method A on an HPLC instrument of the HP1100 series (Agilent) coupled to a Micromass LCZ mass spectrometer. A YMC (Eprogen) column (dimensions: 4.6×33 mm, packed with 1.5 μm ODS II packing material) was employed for the separations. Water/acetonitrile mixtures (each with 0.1% formic acid) were used as mobile phase with a flow rate of 0.8 ml/minute; gradient: 0-90% acetonitrile in 4.5 minutes. Measurement of the UV trace took place at 254 nm.

LC-MS Method C

Data were recorded in analogy to method A on an autopurifier (Waters). An X-bridge (Waters) column (dimensions: 4.6×100 mm, packed with 3.5 μm C18 packing material) was employed for the separations. Water/acetonitrile mixtures (each with 0.1% trifluoroacetic acid) were used as mobile phase with a flow rate of 1.0 ml/minute; gradient: 1-99% acetonitrile in 10 minutes. Measurement of the UV trace took place at 254 nm.

The naming of the chemical structures is in accordance with IUPAC nomenclature.

Preparation of 2,3-dihydro-1-benzothiophen-5-amine 1,1-dioxide

The final compound can be prepared in a five-stage sequence using literature methods starting from 2-chloro-5-nitrobenzaldehyde (*J. Heterocyclic Chem.* 2001, 38, 1025; *J. Am. Chem. Soc.* 1948, 70, 1957; *Rec. Trav. Chim Pays-Bas* 1954, 73, 819).

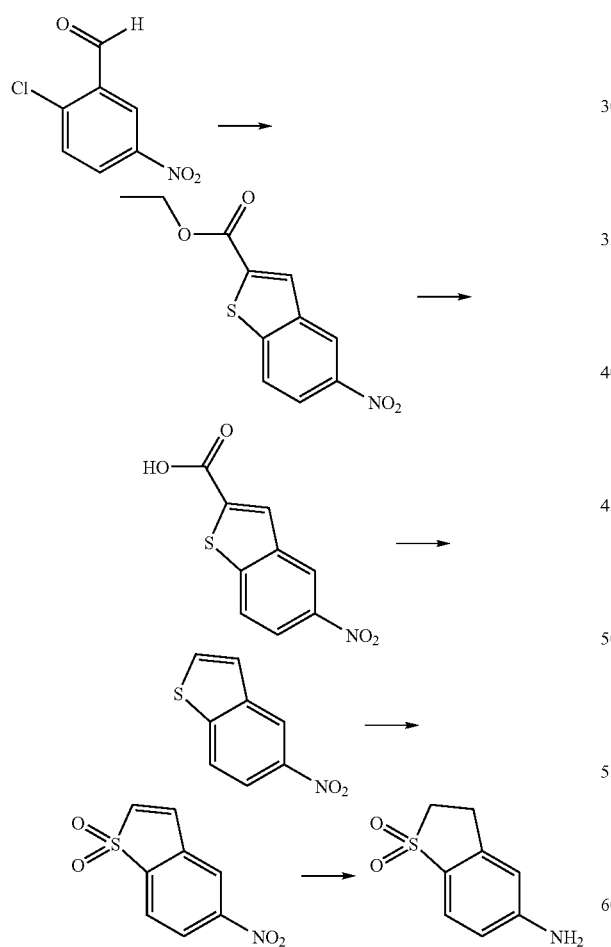

The amine 2 can also be assembled alternatively in accordance with precedents in the literature. 4-Nitrophenol is prepared from 4-chloronitrobenzene as described in *J. Am. Chem. Soc.* 1946, 68, 498-500. Starting therefrom it is possible to assemble the benzothiophene structure by cyclization in the presence of 2-bromoacetaldehyde diethyl acetal (cf. *Bioorq. Med. Chem. Lett.* 2004, 14, 5395-5399).

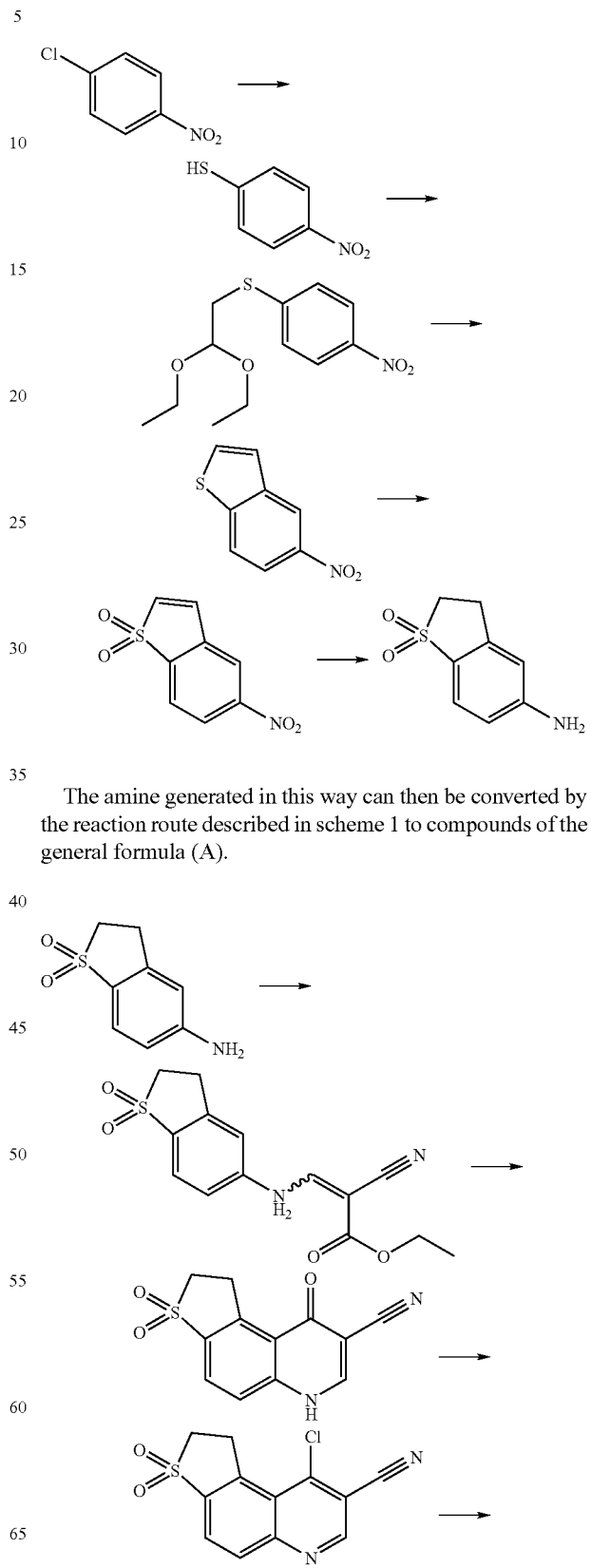

The amine generated in this way can then be converted by the reaction route described in scheme 1 to compounds of the general formula (A).

-continued

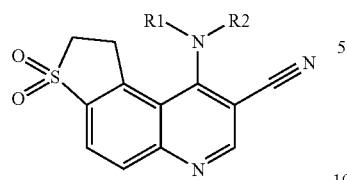

Preparation of ethyl 2-cyano-3-[(1,1-dioxido-2,3-dihydro-1-benzothien-5-yl)amino]acrylate 5 g (27.3 mmol) of 2,3-dihydro-1-benzothiophen-5-amine 1,1-dioxide were suspended in 50 ml of ethanol under argon, 4.62 g (1 eq, 27.3 mmol) of ethyl 2-cyano-3-ethoxyacrylate were added, and the mixture was heated under reflux overnight. For working up, ethyl acetate was added to the mixture, and the precipitate which formed was filtered off with suction on a frit. The solid was dried in vacuo at 50° C. for 1.5 h. 6.87 g (81%) of the target compound were isolated and were employed without further purification in the next stage.

Preparation of 9-oxo-1,2,6,9-tetrahydrothieno[3,2-f] quinoline-8-carbonitrile 3,3-dioxide 1.5 g (0.85 mmol) of ethyl 2-cyano-3-[(1,1-dioxido-2,3-dihydro-1-benzothien-5-yl)amino]acrylate were suspended in 15 ml of Dowtherm A and heated in a metal bath at 290° C. for about 1 h. The reaction mixture was then cooled to RT. The mixture was subsequently mixed with hexane and stirred at RT for 30 min; the precipitate produced thereby was filtered off with suction and washed with hexane. 836 mg (65%) of the desired product were obtained in the form of brownish crystals.

$^1$H-NMR (DMSO-d6): δ=3.62 (m, 2H); 3.86 (m, 2H); 7.68 (d, 1H); 7.99 (d, 1H); 8.77 (s, 1H); 13.06 (s, br, 1H) ppm.

LC-MS (Method A):
Retention time of the product: 0.59 min; mass of the product: m/z=261 ([M+H]$^+$)

Preparation of 9-chloro-1,2-dihydrothieno[3,2-f] quinoline-8-carbonitrile 3,3-dioxide 100 mg (0.38 mmol) of 9-oxo-1,2,6,9-tetrahydrothieno[3,2-f]quinoline-8-carbonitrile 3,3-dioxide are heated in 1 ml of phosphoryl chloride at a bath temperature of about 130° C. for 2 h. The excess phosphoryl chloride is then removed in vacuo, and the crude product is employed without further purification in the next stage.

LC-MS (Method C):
Retention time of the product: 6.78 min; mass of the product: m/z=326 ([M+H]$^+$)

EXAMPLE 1

9-[(3-hydroxy-5-methoxyphenyl)amino]-1,2-dihydrothieno[3,2-f]quinoline-8-carbonitrile 3,3-dioxide 65 mg (0.23 mmol) of 9-chloro-1,2-dihydrothieno[3,2-f]quinoline-8-carbonitrile 3,3-dioxide are refluxed together with 39 mg (1.2 eq., 0.28 mmol) of 3-hydroxy-5-methoxyaniline in 2 ml of isopropanol for 2 hours. After the reaction is complete, the crude product is mixed with water and sat. ammonium chloride solution, extracted 3× with dichloromethane/methanol, washed 1× with sat. sodium chloride solution, dried over sodium sulphate and concentrated in vacuo. Final purification of the compound took place by chromatography. 20 mg (22%) of the desired product were obtained.

LC-MS Method B:
Retention time of the product=1.74 min; MS of the product: m/z=382 ([M+H]$^+$)

The following were prepared in an analogous manner:

TABLE 1

| Example No. | Structure and name | LC/MS-method | Retention time | Mol. weight/ MS (ESI) [M + 1]$^+$ |
|---|---|---|---|---|
| 2 | 9-[(3-methoxyphenyl)amino]-1,2-dihydrothieno[3,2-f]quinoline-8-carbonitrile 3,3-dioxide | A | 0.91 | MW: 365.41 MS (ES+) [M + 1]$^+$: 366 (100%) |

TABLE 1-continued

| Example No. | Structure and name | LC/MS-method | Retention time | Mol. weight/ MS (ESI) [M + 1]+ |
|---|---|---|---|---|
| 3 | 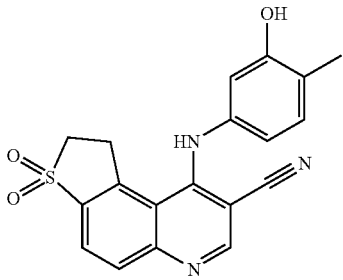<br>9-[(3-hydroxy-4-methylphenyl)amino]-1,2-dihydrothieno[3,2-f]quinoline-8-carbonitrile 3,3-dioxide | B | 1.84 | MW: 365.41<br>MS (ES+)<br>[M + 1]+: 366 (100%) |
| 4 | 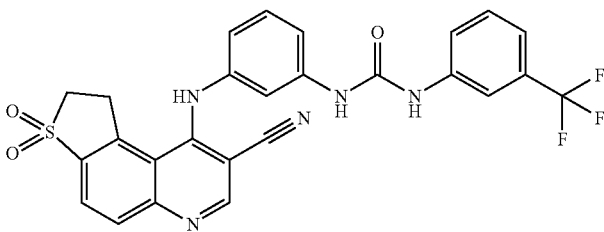<br>1-{3-[(8-cyano-3,3-dioxido-1,2-dihydrothieno[3,2-f]quinolin-9-yl)amino]phenyl}-3-(trifluoromethyl)phenyl]urea | A | 1.18 | MW: 537.52<br>MS (ES+)<br>[M + 1]+: 538 (100%) |
| 5 | 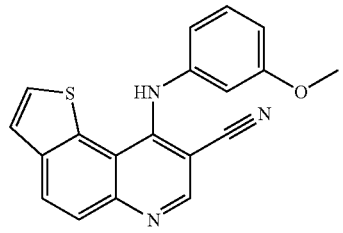<br>9-[(3-methoxyphenyl)amino]thieno[2,3-f]quinoline-8-carbonitrile | A | 2.26 | MW: 331.40<br>MS (ES+)<br>[M + 1]+: 332 (100%) |

The derivatives described in the table below can be prepared in accordance with the reaction route depicted in scheme 1 and the experimental procedures described above:

| Example | Structure |
|---|---|
| 6 | *N-propargyl structure* |
| 7 | *N-cyclopropyl structure* |
| 8 | *N-isopropyl structure* |
| 9 | *N-(but-3-yn-2-yl) structure* |
| 10 | *N-methyl-N-propargyl structure* |
| 11 | *N-(1-cyanoethyl) structure* |
| 12 | *N-(2-cyanoethyl) structure* |
| 13 | *N-(cyclopropylmethyl) structure* |
| 14 | *N-cyclobutyl structure* |
| 15 | *N-tert-butyl structure* |
| 16 | *N-isobutyl structure* |
| 17 | *N-(2-methoxyethyl) structure* |

-continued
| Example | Structure |
|---------|-----------|
| 18 | 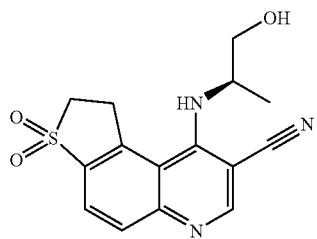 |
| 19 | 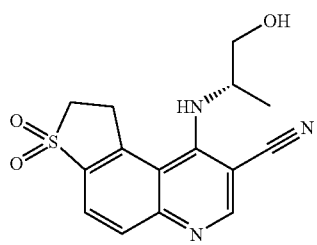 |
| 20 | 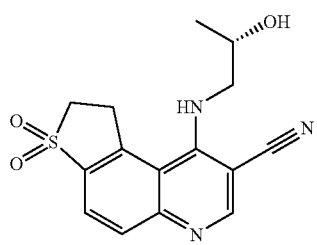 |
| 21 | 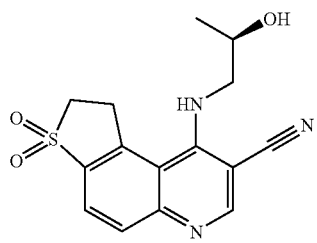 |
| 22 | 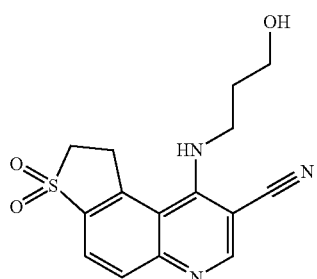 |
| 23 | 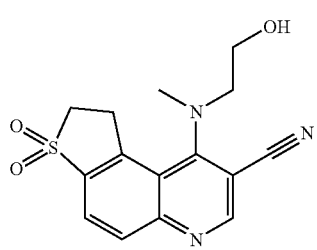 |
-continued
| Example | Structure |
|---------|-----------|
| 24 | 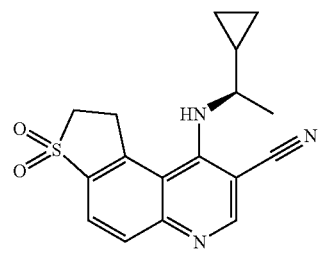 |
| 25 | 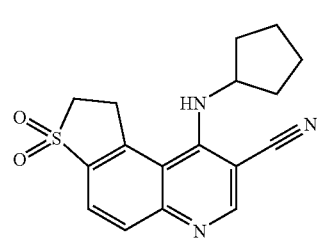 |
| 26 | 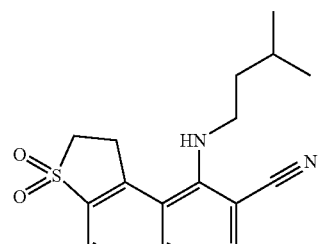 |
| 27 | 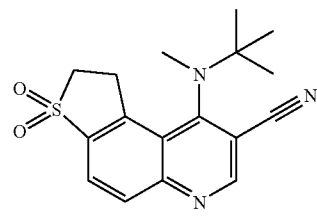 |
| 28 | 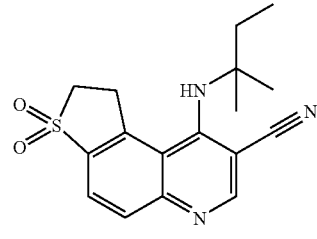 |
| 29 | 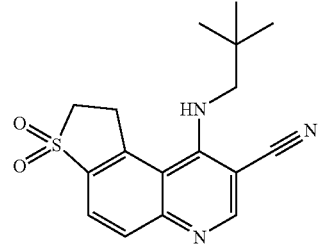 |

-continued
| Example | Structure |
|---------|-----------|
| 30 | 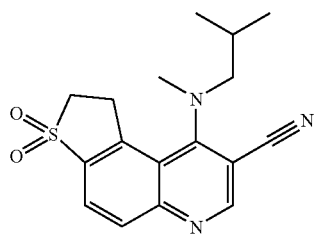 |
| 31 | 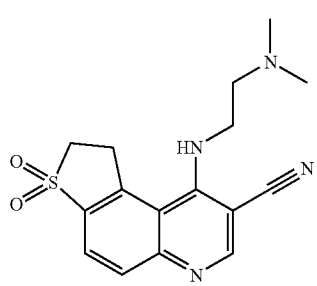 |
| 32 | 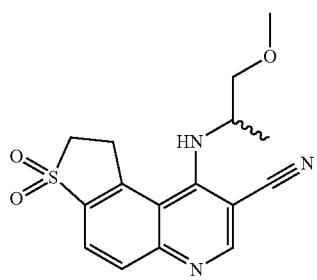 |
| 33 | 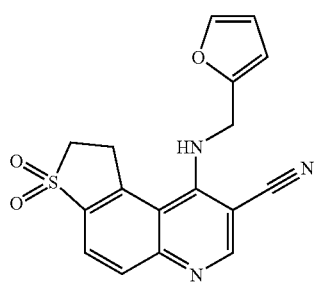 |
| 34 | 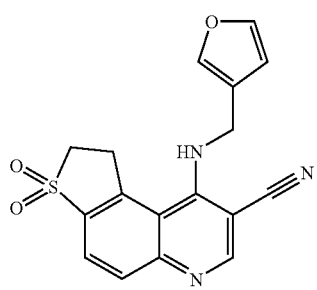 |
-continued
| Example | Structure |
|---------|-----------|
| 35 | 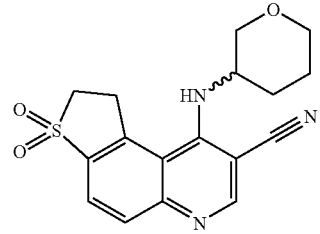 |
| 36 | 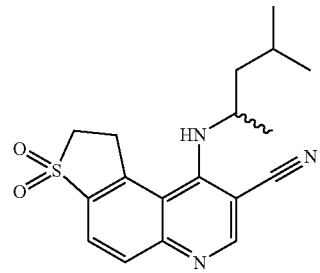 |
| 37 | 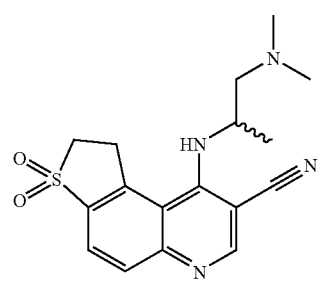 |
| 38 | 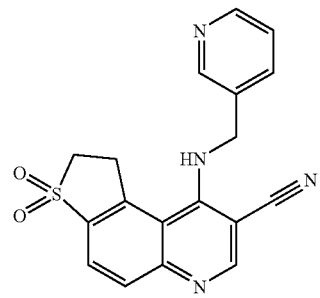 |
| 39 | 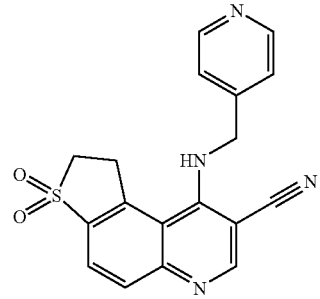 |

-continued
| Example | Structure |
|---|---|
| 40 | 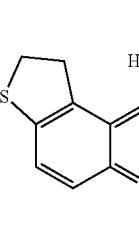 |
| 41 | 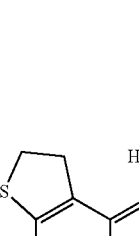 |
| 42 | 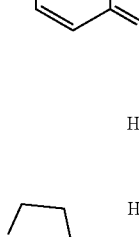 |
| 43 | 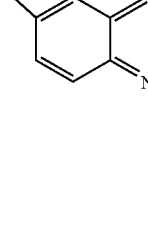 |
| 44 | 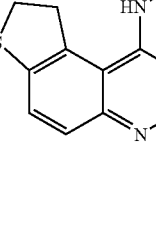 |
-continued
| Example | Structure |
|---|---|
| 45 | 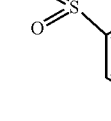 |
| 46 | 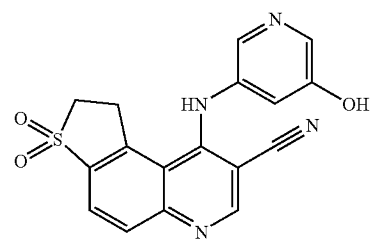 |
| 47 | 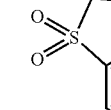 |
| 48 | 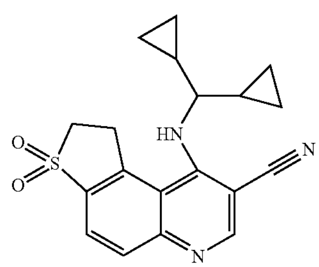 |
| 49 | 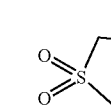 |
| 50 | 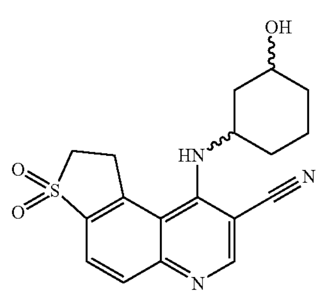 |

-continued
| Example | Structure |
|---|---|
| 51 | 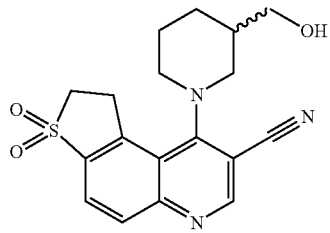 |
| 52 | 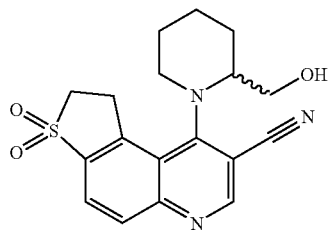 |
| 53 | 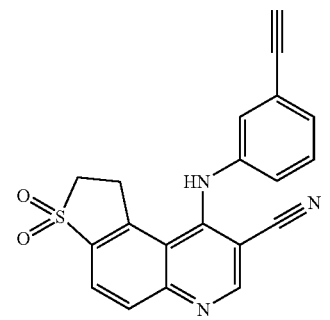 |
| 54 | 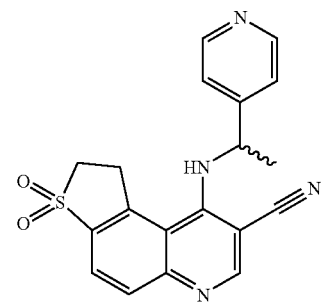 |
| 55 | 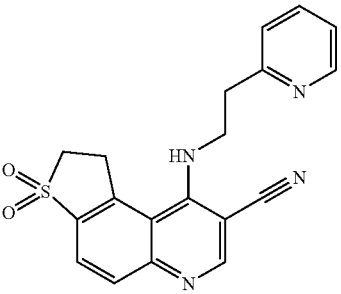 |
-continued
| Example | Structure |
|---|---|
| 56 | 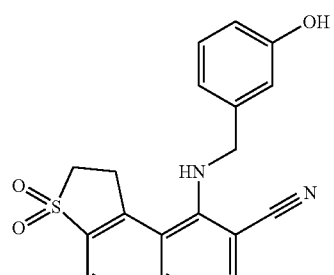 |
| 57 | 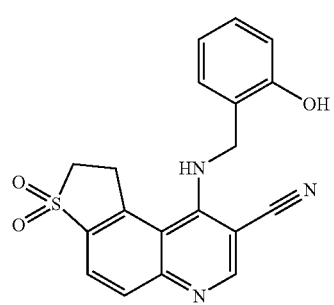 |
| 58 | 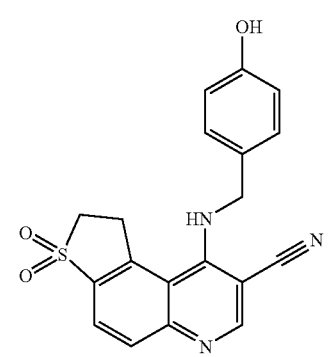 |
| 59 | 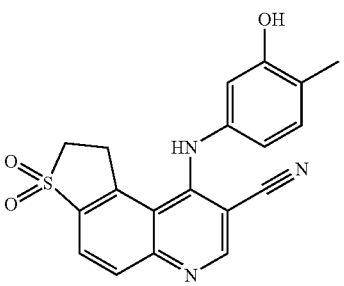 |
| 60 | 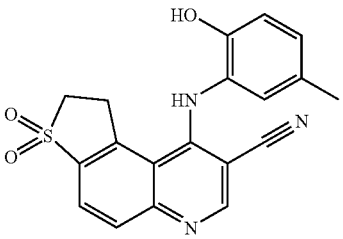 |

-continued
| Example | Structure |
|---|---|
| 61 | 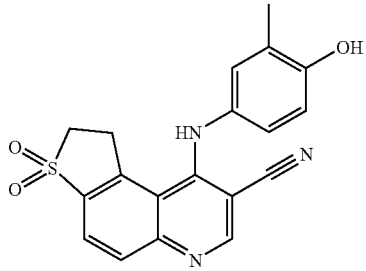 |
| 62 | 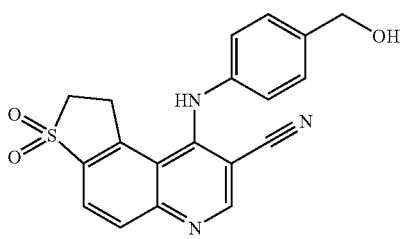 |
| 63 | 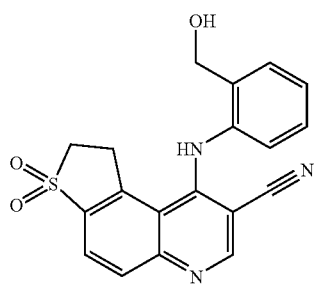 |
| 64 | 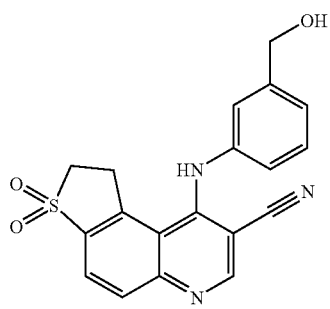 |
| 65 | 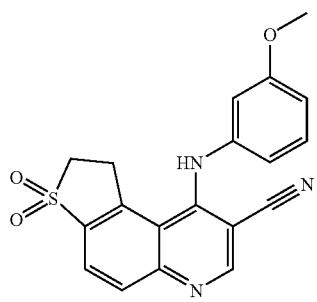 |
-continued
| Example | Structure |
|---|---|
| 66 | 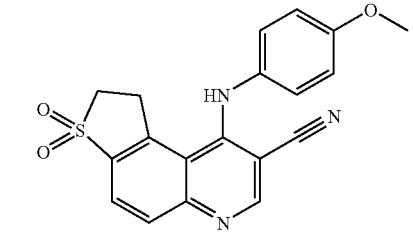 |
| 67 | 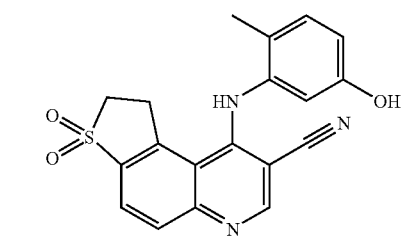 |
| 68 | 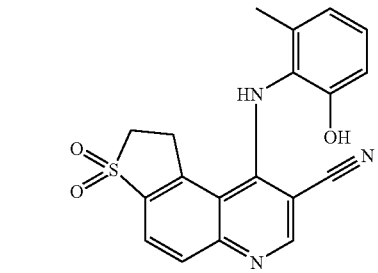 |
| 69 | 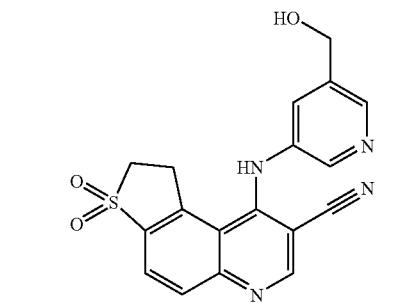 |
| 70 | 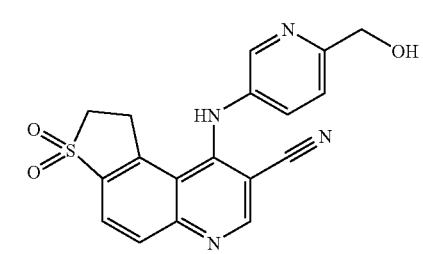 |
| 71 | 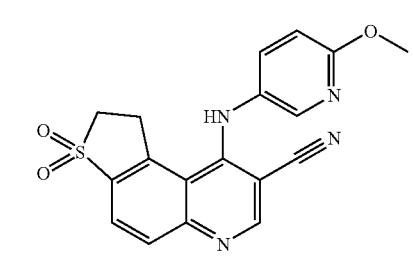 |

-continued

| Example | Structure |
|---------|-----------|
| 72 | 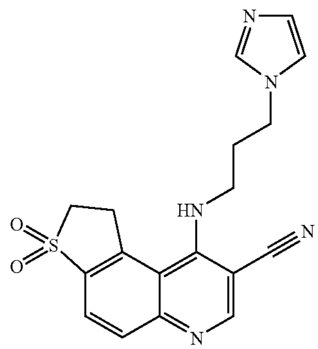 |
| 73 | 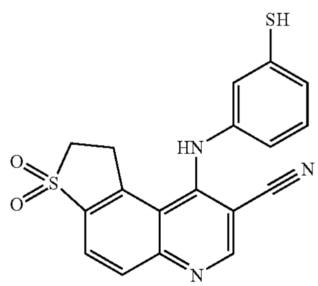 |
| 74 | 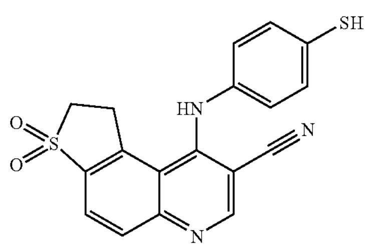 |
| 75 | 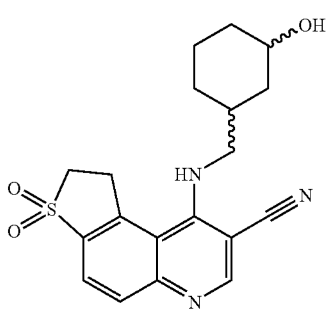 |
| 76 | 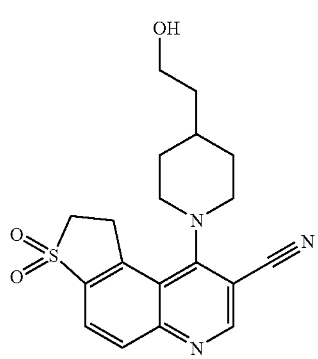 |

-continued

| Example | Structure |
|---------|-----------|
| 77 | 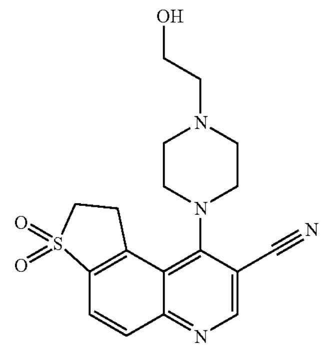 |
| 78 | 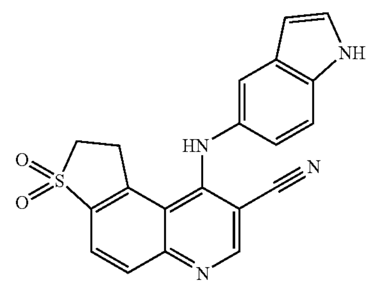 |
| 79 | 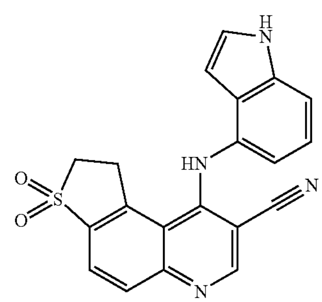 |
| 80 | 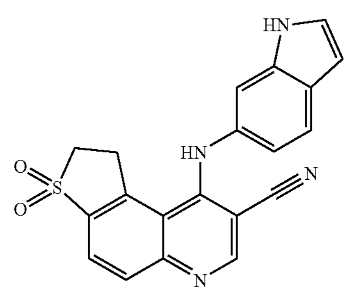 |
| 81 | 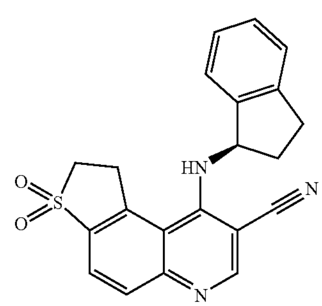 |

-continued

| Example | Structure |
|---|---|
| 82 | 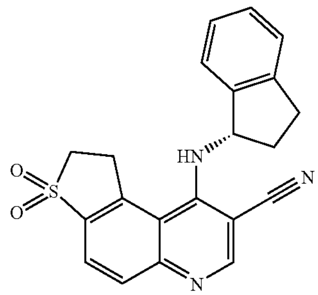 |
| 83 | 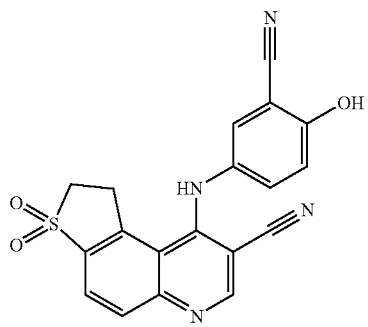 |
| 84 | 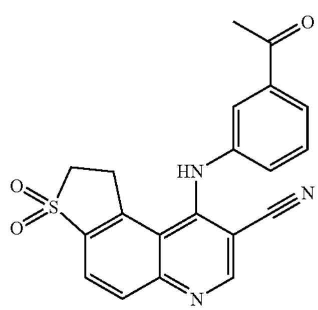 |
| 85 | 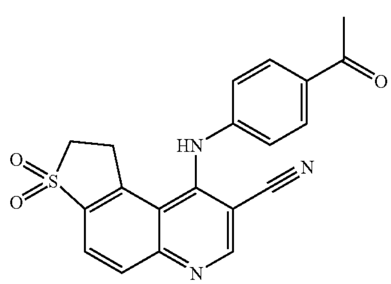 |
| 86 | 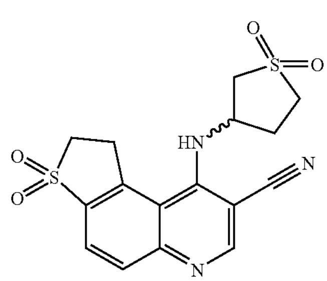 |

-continued

| Example | Structure |
|---|---|
| 87 | 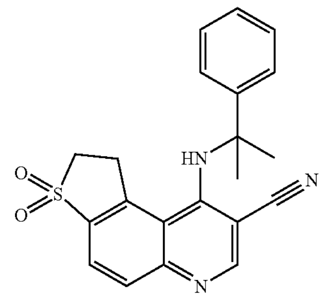 |
| 88 | 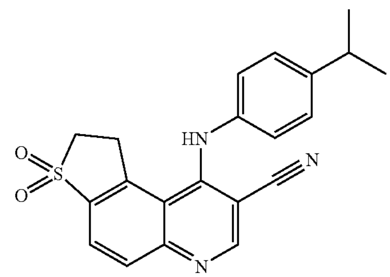 |
| 89 | 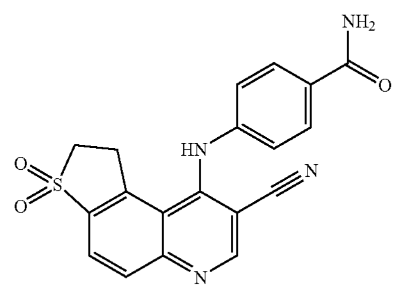 |
| 90 | 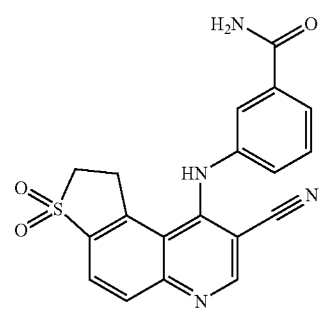 |
| 91 | 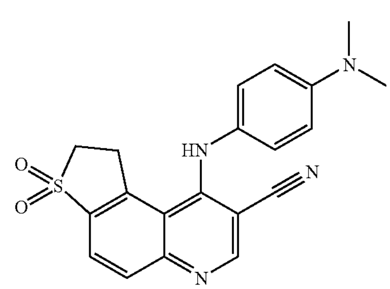 |

-continued

| Example | Structure |
|---------|-----------|
| 92 | 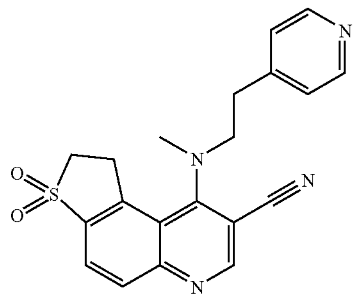 |
| 93 | 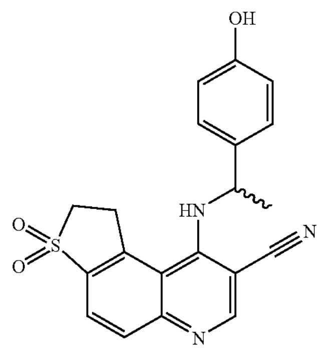 |
| 94 | 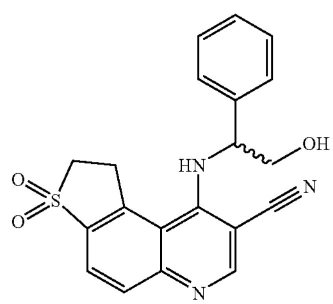 |
| 95 | 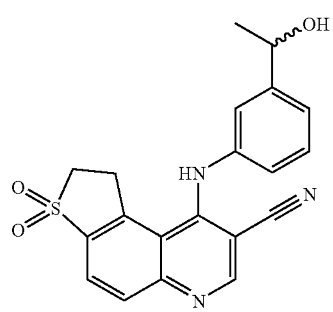 |
| 96 | 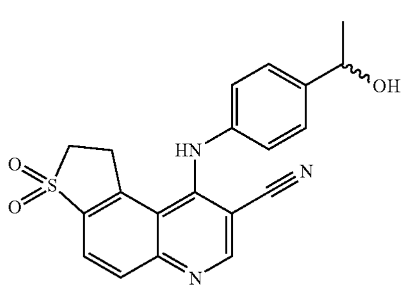 |

-continued

| Example | Structure |
|---------|-----------|
| 97 | 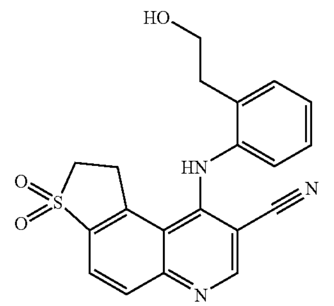 |
| 98 | 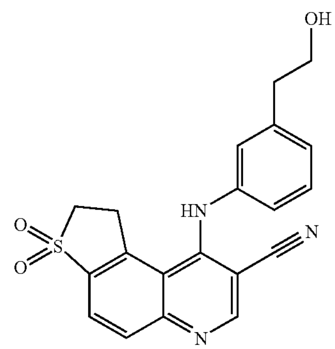 |
| 99 | 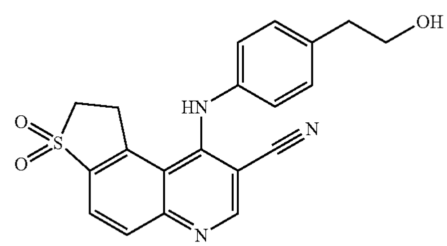 |
| 100 | 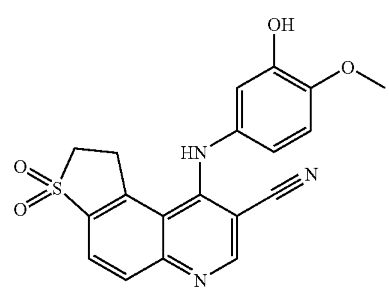 |
| 101 | 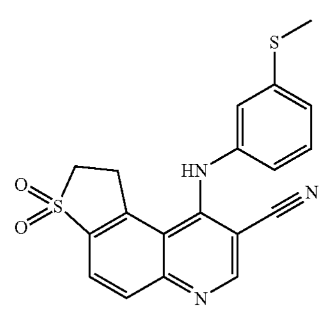 |

-continued
| Example | Structure |
|---|---|
| 102 | 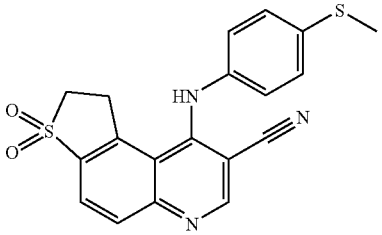 |
| 103 | 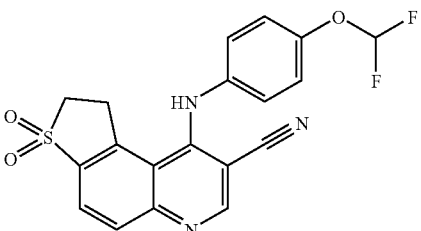 |
| 104 | 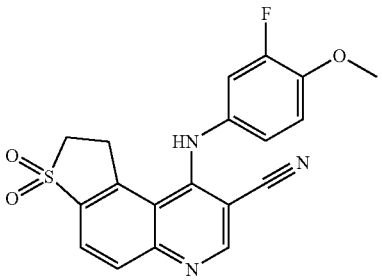 |
| 105 | 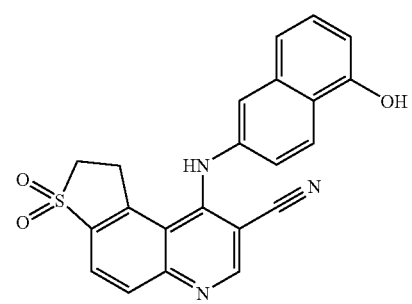 |
| 106 | 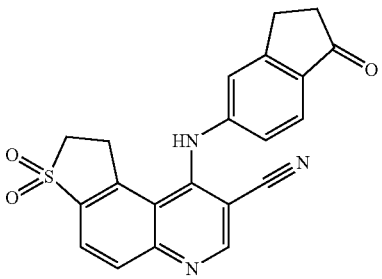 |
-continued
| Example | Structure |
|---|---|
| 107 | 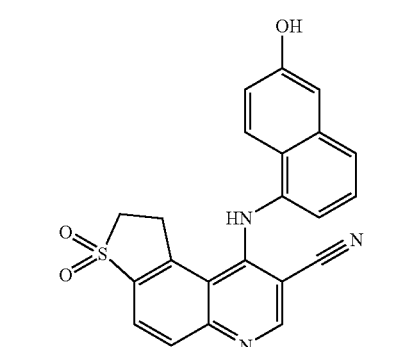 |
| 108 | 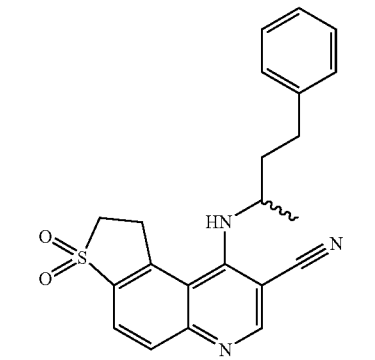 |
| 109 | 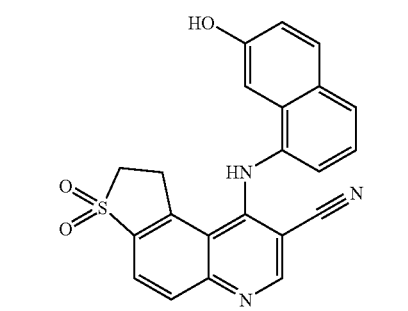 |
| 110 | 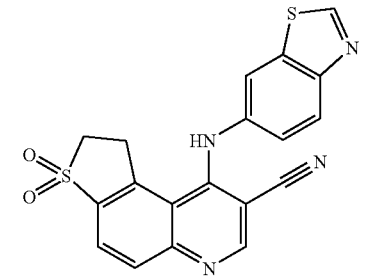 |
| 111 | 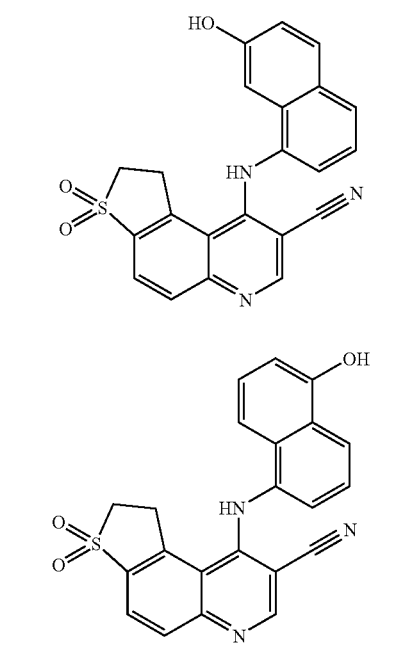 |

Biological Tests on the Compounds

Test System for EphB4

A mixture of 20 ng/ml recombinanter EphB4 kinase (ProQinase GmbH, Freiburg, Germany), 2.67 µg/ml polyGluAlaTyr, 2 µM ATP, 25 mM HEPES (pH 7.3), 5 mM $MgCl_2$, 1 mM $MnCl_2$, 2 mM DTT, 0.1 mM $NaVO_4$, 1% (v/v) glycerol, 0.02% NP40, EDA-free protease inhibitors (Complete from Roche, tablet in 50 ml) is incubated at 20° C. for 10 min. Test substances are dissolved in 100% DMSO and introduced in 0.017 times the volume before the start of the reaction. 60 minutes after addition of 1.7 times the volume of a solution of 50 mM Hepes pH 7.0, 0.2% BSA, 0.14 µg/ml PT66-Europium, 3.84 µg/ml SA-XL665, 75 mM EDTA, the mixture is measured in a Perkin-Elmer Discovery HTRF measuring instrument.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 006 445.9, filed Jun. 21, 2006, and U.S. Provisional Application Ser. No. 60/816,628, filed Jun. 27, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A quinoline compound of formula (A):

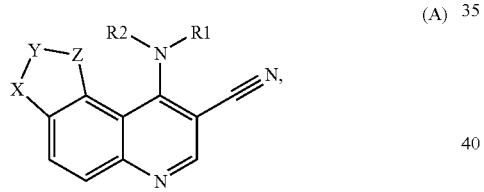

(A)

wherein
$R^1$ and $R^2$ are identical or different and are each, independently of one another, hydrogen, hydroxy, halogen, nitro, cyano, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p PO_3(R^6)_2$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^5(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, or —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are in each case unsubstituted or substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$, or —$OR^5$, where the carbon framework of the —$C_3$-$C_{10}$-cycloalkyl and of the —$C_1$-$C_{10}$-alkyl groups optionally include, independently of one another, one or more nitrogen atoms, oxygen atoms, sulphur atoms, —$NR^4$ groups, or C=O groups, or optionally include one or more double bonds, and where the phenyl radical is optionally substituted one or more times independently of one another by hydroxy, halogen, nitro, cyano, phenyl, —$NR^5R^6$, alkyl or —$OR^5$; or $R^1$ and $R^2$ form together a bridge of 3-10 methylene units, where up to two methylene units are each optionally replaced by O, S or —$NR^4$;

X, Y, Z are identical or different and are each, independently of one another, —$CR^3$=, —$CR^3R^4$—, —$C(O)$—, —$N$=, —$S$—, —$O$—, —$NR^3$—, —$S(O)_2$—, —$S(O)$—, or —$S(O)(N$=$R^3)$—, and single or double bonds are present between X, Y and Z, wherein a maximum of one of X, Y and Z is —$O$—, and at most one of X, Y and Z is —$N$= or —$NR^3$—;

$R^3$ and $R^4$ are each, independently of one another, hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl are in each case, independently of one another, unsubstituted or substituted one or more times by hydroxy, halogen, nitro, cyano, phenyl, —$NR^5R^6$, alkyl, —$SR^5$, or —$OR^5$, $R^5$ and $R^6$ are identical or different and are each, independently of one another, hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, or —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are in each case, independently of one another, unsubstituted or substituted one or more times by hydroxy, halogen, cyano, nitro, —$OR^7$, —$NR^7R^8$, —$C(O)NR^7R^8$, —$C(O)OR^7$, or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or $R^5$ and $R^6$ together form a bridge of 3-10 methylene units, where up to two methylene units are each optionally replaced by O, S or $NR^4$;

$R^7$ and $R^8$ are identical or different and are each, independently of one another, hydrogen, —$C_1$-$C_4$-alkyl, —$C_6$-$C_{12}$-aryl, or —$C_5$-$C_{18}$-heteroaryl, where alkyl, aryl, and heteroaryl are each, independently of one another, unsubstituted or substituted one or more times by halogen or alkoxy, or $R^7$ and $R^8$ together form a bridge of 3-10 methylene units, where up to two methylene units are each optionally replaced by O, S or —$NR^4$;

m', m" are independently of one another 0, 1, 2, 3, or 4, n is 1, 2, 3, 4, 5, or 6, and p is 0, 1, 2, 3, 4, 5, or 6; or an N-oxide, stereoisomer, diastereomer, enantiomer or salt thereof.

2. A quinoline compound according to claim 1, wherein:

$R^1$ and $R^2$ are identical or different and are each, independently of one another, hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —(CH$_2$)$_n$—$C_6$-$C_{12}$-aryl, —(CH$_2$)$_n$—$C_5$-$C_{18}$-heteroaryl, —(CH$_2$)$_n$—$C_3$-$C_{10}$-cycloalkyl, —(CH$_2$)$_n$—$C_3$-$C_{12}$-heterocycloalkyl, -phenylene-(CH$_2$)$_p$—$R^6$, —(CH$_2$)$_p$—NR$^5$R$^6$, —(CH$_2$)$_p$—NR$^4$COR$^5$, —(CH$_2$)$_p$—NR$^4$CSR$^5$, —(CH$_2$)$_p$—NR$^4$S(O)R$^5$, —(CH$_2$)$_p$—NR$^4$S(O)$_2$R$^5$, —(CH$_2$)$_p$—NR$^4$CONR$^5$R$^6$, —(CH$_2$)$_p$—NR$^4$COOR$^5$, —(CH$_2$)$_p$—NR$^4$C(NH)NR$^5$R$^6$, —(CH$_2$)$_p$—NR$^4$CSNR$^5$R$^6$, —(CH$_2$)$_p$—NR$^4$S(O)NR$^5$R$^6$, —(CH$_2$)$_p$—NR$^4$S(O)$_2$NR$^5$R$^6$, —(CH$_2$)$_p$—COR$^5$, —(CH$_2$)$_p$—CSR$^5$, —(CH$_2$)$_p$—S(O)R$^5$, —(CH$_2$)$_p$—S(O)(NH)R$^5$, —(CH$_2$)$_p$—S(O)$_2$R$^5$, —(CH$_2$)$_p$—S(O)$_2$NR$^5$R$^6$, —(CH$_2$)$_p$—SO$_2$OR$^5$, —(CH$_2$)$_p$—CO$_2$R$^5$, —(CH$_2$)$_p$—CONR$^5$R$^6$, —(CH$_2$)$_p$—CSNR$^5$R$^6$, —OR$^5$, —CHR$^5$R$^6$, —(CH$_2$)$_p$—SR$^5$, or —CR$^5$(OH)—R$^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are in each case, independently of one another, unsubstituted or substituted one or more times by hydroxy, halogen, nitro, cyano, —NR$^5$R$^6$, —C(O)NR$^5$R$^6$, —S(O)NR$^5$R$^6$, —NR$^5$S(O)$_2$R$^6$, —NR$^5$C(O)R$^6$, —SR$^5$R$^5$ or —OR$^5$, where the carbon framework of the —$C_3$-$C_{10}$-cycloalkyl and of the —$C_1$-$C_{10}$-alkyl groups optionally include, independently of one another, one or more nitrogen atoms, oxygen atoms, sulphur atoms, —NR$^4$ groups, or C=O groups, or optionally include one or more double bonds, where the phenyl radical is optionally substituted one or more times independently of one another by hydroxy, halogen, nitro, cyano, phenyl, —NR$^5$R$^6$, alkyl or —OR$^5$, or $R^1$ and $R^2$ optionally together form a bridge of 3-10 methylene units, where up to two methylene units are optionally replaced by O, S or —NR$^4$;

X, Y, Z are identical or different and are each, independently of one another, —CR$^3$=, —CR$^3$R$^4$—, —C(O)—, —N=, —S—, —O—, —NR$^3$—, —S(O)$_2$—, —S(O)—, or —S(O)(N=R$^3$)—, and single or double bonds are present between X, Y and Z, b wherein a maximum of one of X, Y and Z is —O—, and at most one of X, Y and Z is —N= or —NR$^3$—;

$R^3$ and $R^4$ are each, independently of one another, hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl are in each case, independently of one another, unsubstituted or substituted one or more times by hydroxy, halogen, nitro, cyano, phenyl, —NR$^5$R$^6$, alkyl, —SR$^5$, or —OR$^5$, $R^5$ and $R^6$ are identical or different and are each, independently of one another, hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, or —$C_5$-$C_{18}$-heteroaryl are in each case, independently of one another, unsubstituted or substituted one or more times by hydroxy, halogen, cyano, nitro, —OR$^7$, —NR$^7$R$^8$, —C(O)NR$^7$R$^8$, —C(O)OR$^7$, or —$C_1$-$C_6$-alkyl, where —$C_1$-$C_6$-alkyl is unsubstituted or is substituted one or more times independently of one another by halogen, hydroxy, cyano, —NR$^7$R$^8$, —OR$^7$, or phenyl; or $R^5$ and $R^6$ together form a bridge of 3-10 methylene units, wherein up to two methylene units are each optionally replaced by O, S or NR$^4$;

$R^7$ and $R^8$ are identical or different and are each, independently of one another, hydrogen, —$C_1$-$C_4$-alkyl, —$C_6$-$C_{12}$-aryl, or —$C_5$-$C_{18}$-heteroaryl, where alkyl, aryl, and heteroaryl in each case are unsubstituted or substituted one or more times independently of one another by halogen or alkoxy, or $R^7$ and $R^8$ together form a bridge of 3-10 methylene units, wherein up to two methylene units are each optionally replaced by O, S or —NR$^4$;

m', m" are independently of one another 0, 1, 2, 3, or 4, n is 1, 2, 3, 4, 5, or 6, p is 0, 1, 2, 3, 4, 5, or 6; or an N-oxide, stereoisomer, diastereomer, enantiomer or salt thereof.

3. A quinoline compound according to claim 1, wherein said compound is of formulae (A1-A5):

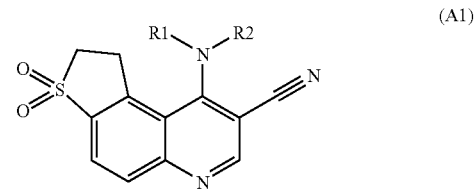

(A1)

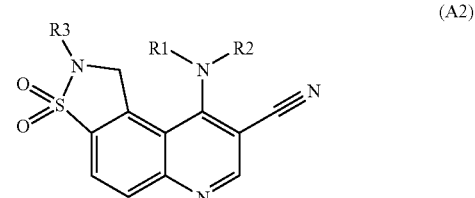

(A2)

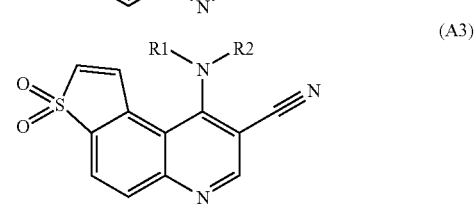

(A3)

-continued

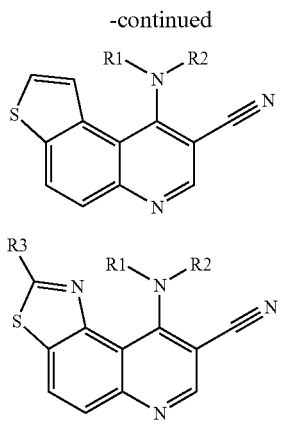

wherein:

R¹ and R² are identical or different and are each, independently of one another, hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—$R^6$, —$(CH_2)_p$—$NR^5R^6$, —$(CH_2)_p$—$NR^4COR^5$, —$(CH_2)_p$—$NR^4CSR^5$, —$(CH_2)_p$—$NR^4S(O)R^5$, —$(CH_2)_p$—$NR^4S(O)_2R^5$, —$(CH_2)_p$—$NR^4CONR^5R^6$, —$(CH_2)_p$—$NR^4COOR^5$, —$(CH_2)_p$—$NR^4C(NH)NR^5R^6$, —$(CH_2)_p$—$NR^4CSNR^5R^6$, —$(CH_2)_p$—$NR^4S(O)NR^5R^6$, —$(CH_2)_p$—$NR^4S(O)_2NR^5R^6$, —$(CH_2)_p$—$COR^5$, —$(CH_2)_p$—$CSR^5$, —$(CH_2)_p$—$S(O)R^5$, —$(CH_2)_p$—$S(O)(NH)R^5$, —$(CH_2)_p$—$S(O)_2R^5$, —$(CH_2)_p$—$S(O)_2NR^5R^6$, —$(CH_2)_p$—$SO_2OR^5$, —$(CH_2)_p$—$CO_2R^5$, —$(CH_2)_p$—$CONR^5R^6$, —$(CH_2)_p$—$CSNR^5R^6$, —$OR^5$, —$CHR^5R^6$, —$(CH_2)_p$—$SR^5$, or —$CR^5(OH)$—$R^6$, where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are in each case unsubstituted or substituted one or more times independently of one another by hydroxy, halogen, nitro, cyano, —$NR^5R^6$, —$C(O)NR^5R^6$, —$S(O)_2NR^5R^6$, —$NR^5S(O)_2R^6$, —$NR^5C(O)R^6$, —$SR^5$, —$R^5$ or —$OR^5$, where the carbon framework of the —$C_3$-$C_{10}$-cycloalkyl and of the —$C_1$-$C_{10}$-alkyl groups optionally include, independently of one another, one or more nitrogen atoms, oxygen atoms, sulphur atoms, —$NR^4$ groups, or C=O groups, or optionally include one or more double bonds, and where the phenyl radical is optionally substituted one or more times independently of one another by hydroxy, halogen, nitro, cyano, phenyl, —$NR^5R^6$, alkyl or —$OR^5$; or R¹ and R² optionally together form a bridge of 3-10 methylene units, where up to two methylene units are each optionally replaced by O, S or —$NR^4$;

R³ and R⁴ are each, independently of one another, hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl are independently of one another unsubstituted or substituted one or more times by hydroxy, halogen, nitro, cyano, phenyl, —$NR^5R^6$, alkyl, —$SR^5$ or —$OR^5$, R⁵ and R⁶ are identical or different and are each, independently of one another, hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, or —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are independently of one another unsubstituted or are substituted one or more times by hydroxy, halogen, cyano, nitro, —$OR^7$, —$NR^7R^8$, —$C(O)NR^7R^8$, —$C(O)OR^7$ or —$C_1$-$C_6$-alkyl, where —$C_1$-$C_6$-alkyl is unsubstituted or is substituted one or more times independently of one another by halogen, hydroxy, cyano, —$NR^7R^8$, —$OR^7$ or phenyl; or R⁵ and R⁶ together form a bridge of 3-10 methylene units, wherein up to two methylene units are each optionally replaced by O, S or $NR^4$;

R⁷, R⁸ are identical or different and are each, independently of one another, hydrogen, —$C_1$-$C_4$-alkyl, —$C_6$-$C_{12}$-aryl, or —$C_5$-$C_{18}$-heteroaryl, where alkyl, aryl, and heteroaryl are in each case unsubstituted or substituted one or more times independently of one another by halogen or alkoxy, or R⁷ and R⁸ together form a bridge of 3-10 methylene units, wherein up to two methylene units are each optionally replaced by O, S or $NR^4$;

m', m" and independently of one another 0, 1, 2, 3, or 4, n is 1, 2, 3, 4, 5, or 6, p is 0, 1, 2, 3, 4, 5, or 6; or an N-oxide, stereoisomer, diastereomer, enantiomer or salt thereof.

4. A quinoline compound according to claim 1, wherein said compound is of formulae (A1-A5):

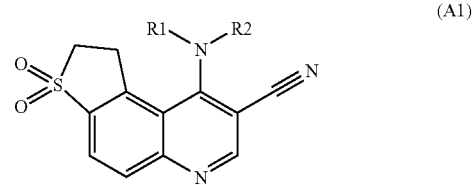

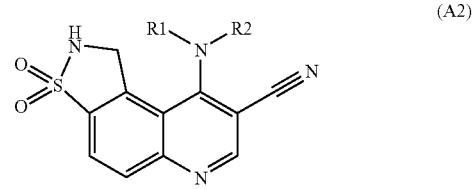

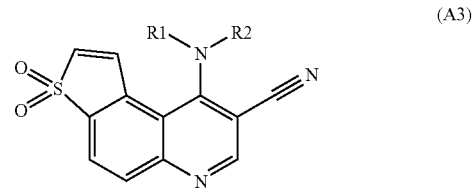

-continued

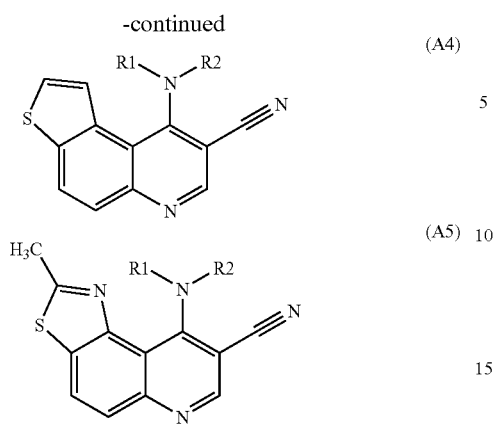

where:
R[1] and R[2] are identical or different and are each, independently of one another, hydrogen, —$C_1$-$C_6$-alkyl, —$C_1$-$C_4$-hydroxyalkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, —$C_1$-$C_6$-alkoxy, —$C_1$-$C_6$-alkoxy-$C_1$-$C_6$-alkoxy, —$C_1$-$C_6$-alkoxy-$C_1$-$C_6$-alkyl, —$C_1$-$C_6$-alkoxy-$C_1$-$C_6$-alkoxy-$C_1$-$C_6$-alkyl, —$(CH_2)_n$—$C_6$-$C_{12}$-aryl, —$(CH_2)_n$—$C_5$-$C_{18}$-heteroaryl, —$(CH_2)_n$—$C_3$-$C_{10}$-cycloalkyl, —$(CH_2)_n$—$C_3$-$C_{12}$-heterocycloalkyl, -phenylene-$(CH_2)_p$—R[6], —$(CH_2)_p$—NR[5]R[6], —$(CH_2)_p$—NR[4]COR[5], —$(CH_2)_p$—NR[4]CSR[5], —$(CH_2)_p$—NR[4]S(O)R[5], —$(CH_2)_p$—NR[4]S(O)$_2$R[5], —$(CH_2)_p$—NR[4]CONR[5]R[6], —$(CH_2)_p$—NR[4]COOR[5], —$(CH_2)_p$—NR[4]C(NH)NR[5]R[6], —$(CH_2)_p$—NR[4]CSNR[5]R[6], —$(CH_2)_p$—NR[4]S(O)NR[5]R[6], —$(CH_2)_p$—NR[4]S(O)$_2$NR[5]R[6], —$(CH_2)_p$—COR[5], —$(CH_2)_p$—CSR[5], —$(CH_2)_p$—S(O)R[5], —$(CH_2)_p$—S(O)(NH)R[5], —$(CH_2)_p$—S(O)$_2$R[5], —$(CH_2)_p$—S(O)$_2$NR[5]R[6], —$(CH_2)_p$—SO$_2$OR[5], —$(CH_2)_p$—CO$_2$R[5], —$(CH_2)_p$—CONR[5]R[6], —$(CH_2)_p$—CSNR[5]R[6], —OR[5], —CHR[5]R[6], —$(CH_2)_p$—SR[5], or —CR[5](OH)—R[6],
where —$C_1$-$C_6$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, —$C_6$-$C_{12}$-aryl, —$C_5$-$C_{18}$-heteroaryl, and —$C_1$-$C_6$-alkoxy are each independently of one another, unsubstituted or substituted one or more times by hydroxy, halogen, nitro, cyano, —NR[5]R[6], —C(O)NR[5]R[6], —S(O)$_2$NR[5]R[6], —NR[5]S(O)$_2$R[6], —NR[5]C(O)R[6], —SR[5], —R[5] or —OR[5],
where the carbon framework of the —$C_3$-$C_{10}$-cycloalkyl and of the —$C_1$-$C_{10}$-alkyl optionally comprise one or more times independently of one another nitrogen, oxygen, sulphur atoms, —NR[4] or C=O groups or one or more double bonds, and
where the phenyl radical is optionally substituted one or more times independently of one another by hydroxy, halogen, nitro, cyano, phenyl, —NR[5]R[6], alkyl, or —OR[5], or R[1] and R[2] together form a bridge of 3-10 methylene units, where up to two methylene units are each optionally replaced by O, S or —NR[4];

R[4] is hydrogen, —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, or —$C_1$-$C_{10}$-alkanoyl, where —$C_1$-$C_{10}$-alkyl, —$C_2$-$C_6$-alkenyl, —$C_2$-$C_6$-alkynyl, —$C_3$-$C_{10}$-cycloalkyl, —$C_3$-$C_{12}$-heterocycloalkyl, and —$C_1$-$C_{10}$-alkanoyl are each, independently of one another, unsubstituted or substituted one or more times independently of one another by hydroxy, halogen, nitro, cyano, phenyl, —NR[5]R[6], alkyl, —SR[5] or —OR[5], R[5] and R[6] are identical or different and are each, independently of one another, hydrogen, —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, or —$C_5$-$C_{18}$-heteroaryl, where —$C_1$-$C_{10}$-alkyl, —$C_2$-$C_{10}$-alkenyl, —$C_2$-$C_{10}$-alkynyl, —$C_1$-$C_6$-alkoxy, —$C_3$-$C_{10}$-cycloalkyl, —$C_3$-$C_{12}$-heterocycloalkyl, —$C_6$-$C_{12}$-aryl, and —$C_5$-$C_{18}$-heteroaryl are each, independently of one another, unsubstituted or substituted one or more times by hydroxy, halogen, cyano, nitro, —OR[7], —NR[7]R[8], —C(O)NR[7]R[8], —C(O)OR[7] or —$C_1$-$C_6$-alkyl, where —$C_1$-$C_6$-alkyl is unsubstituted or is substituted one or more times independently of one another by halogen, hydroxy, cyano, —NR[7]R[8], —OR[7] or phenyl; or R[5] and R[6] together form a bridge of 3-10 methylene units, where up to two methylene units are each optionally replaced by O, S or NR[4];

R[7], R[8] are identical or different and are each, independently of one another, hydrogen, —$C_1$-$C_4$-alkyl, —$C_6$-$C_{12}$-aryl, or —$C_5$-$C_{18}$-heteroaryl, where alkyl, aryl, and heteroaryl are in each case unsubstituted or substituted one or more times independently of one another by halogen or alkoxy, or R[7] and R[8] together form a bridge of 3-10 methylene units, where up to two methylene units are each optionally replaced by O, S or —NR[4];

m', m" are, independently of one another, 0, 1, 2, 3, or 4,
n is 1, 2, 3, 4, 5, or 6,
p is 0, 1, 2, 3, 4, 5, or 6; or
an N-oxide, hydrate, stereoisomer, diastereomer, enantiomer or salt thereof.

5. A quinoline compound according to claim 1, wherein said compound is:
9-[(3-hydroxy-5-methoxyphenyl)amino]-1,2-dihydrothieno[3,2-f]quinoline-8-carbonitrile 3,3-dioxide or a physiologically tolerated salt thereof;
9-[(3-methoxyphenyl)amino]-1,2-dihydrothieno[3,2-f]quinoline-8-carbonitrile 3,3-dioxide or a physiologically tolerated salt thereof;
9-[(3-hydroxy-4-methylphenyl)amino]-1,2-dihydrothieno[3,2-f]quinoline-8-carbonitrile 3,3-dioxide or a physiologically tolerated salt thereof;
1-{3-[(8-cyano-3,3-dioxido-1,2-dihydrothieno[3,2-f]quinolin-9-yl)amino]phenyl}-3-[3-(trifluoromethyl)phenyl]urea or a physiologically tolerated salt thereof; or
9-[(3-methoxyphenyl)amino]thieno[2,3-f]quinoline-8-carbonitrile or a physiologically tolerated salt thereof.

6. A process for preparing a quinoline compound according to claim 1, said process comprising:

reacting an intermediate of formula V:

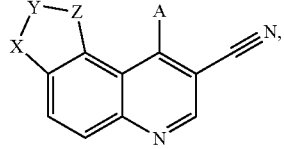

(V)

wherein A is a leaving group, with a reagent of formula V':

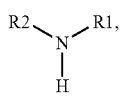

(V')

to give a compound of formula (A):

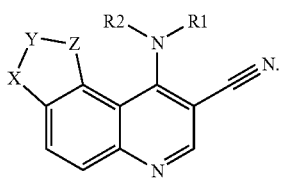

(A)

7. A pharmaceutical composition comprising a compound according to claim 1, and an inert carrier material suitable for enteral, parenteral, or oral administration.

8. A pharmaceutical composition comprising a compound according to claim 1, and at least one suitable formulation substance or carrier.

9. A compound according to claim 1, wherein cycloalkyls have 3 to 6 carbon atoms.

10. A compound according to claim 1, wherein $C_6$-$C_{12}$-aryl are in each case phenyl, naphthyl, or biphenyl.

11. A compound according to claim 1, wherein heteroaryl groups have 5 to 10 ring atoms and the heteroatoms thereof are in each case O, S, or N.

12. A compound according to claim 1, wherein heteroaryl groups are in each case thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl, 1,3-benzodioxolyl, benzofuranyl, benzothienyl, benzoxazolyl, benzimidazolyl, indazolyl, indolyl, isoindolyl, oxepinyl, azocinyl, indolizinyl, indolyl, isoindolyl, indazolyl, benzimidazolyl, purinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, or xanthenyl.

13. A compound according to claim 1, wherein $C_3$-$C_{12}$-heterocycloalkyl groups are in each case oxiranyl, oxetanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, or quinuclidinyl.

14. A compound according to claim 1, wherein said compound is selected from:

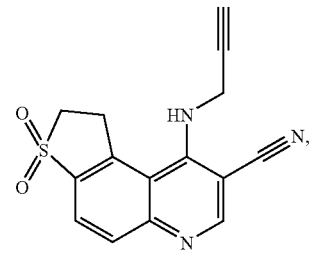

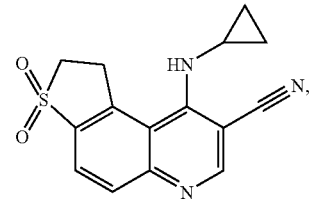

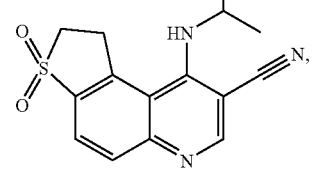

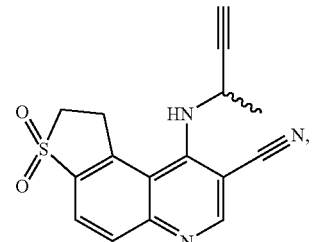

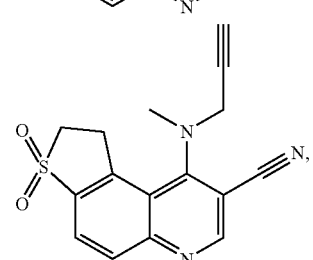

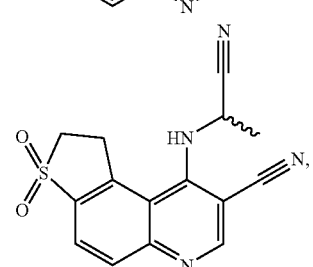

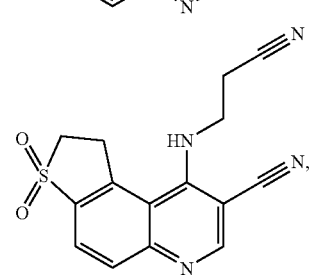

57
-continued
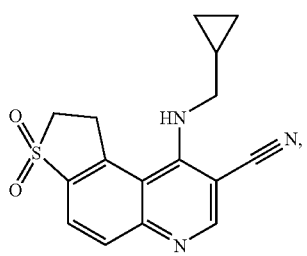
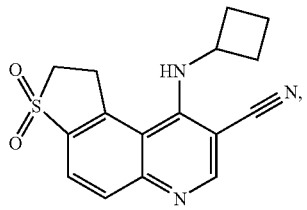
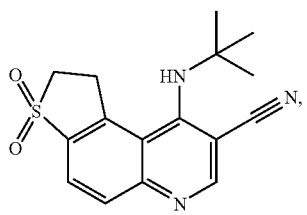
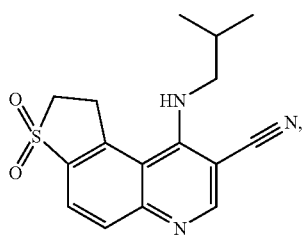
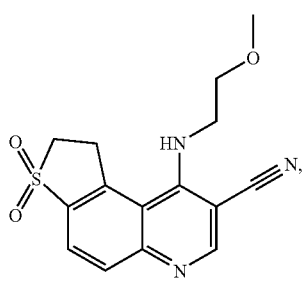
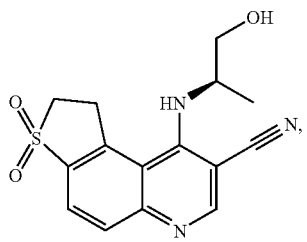
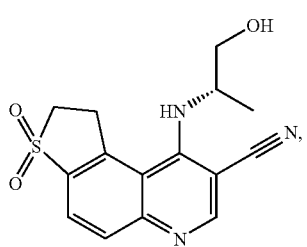
58
-continued
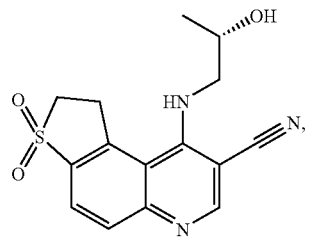
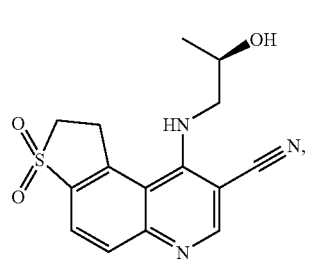
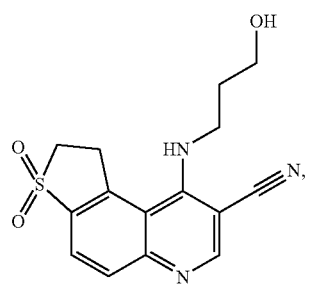
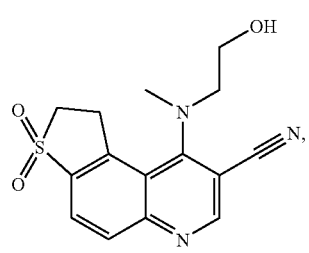
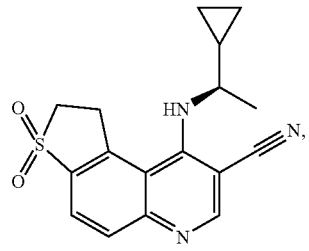
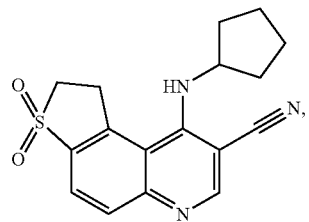

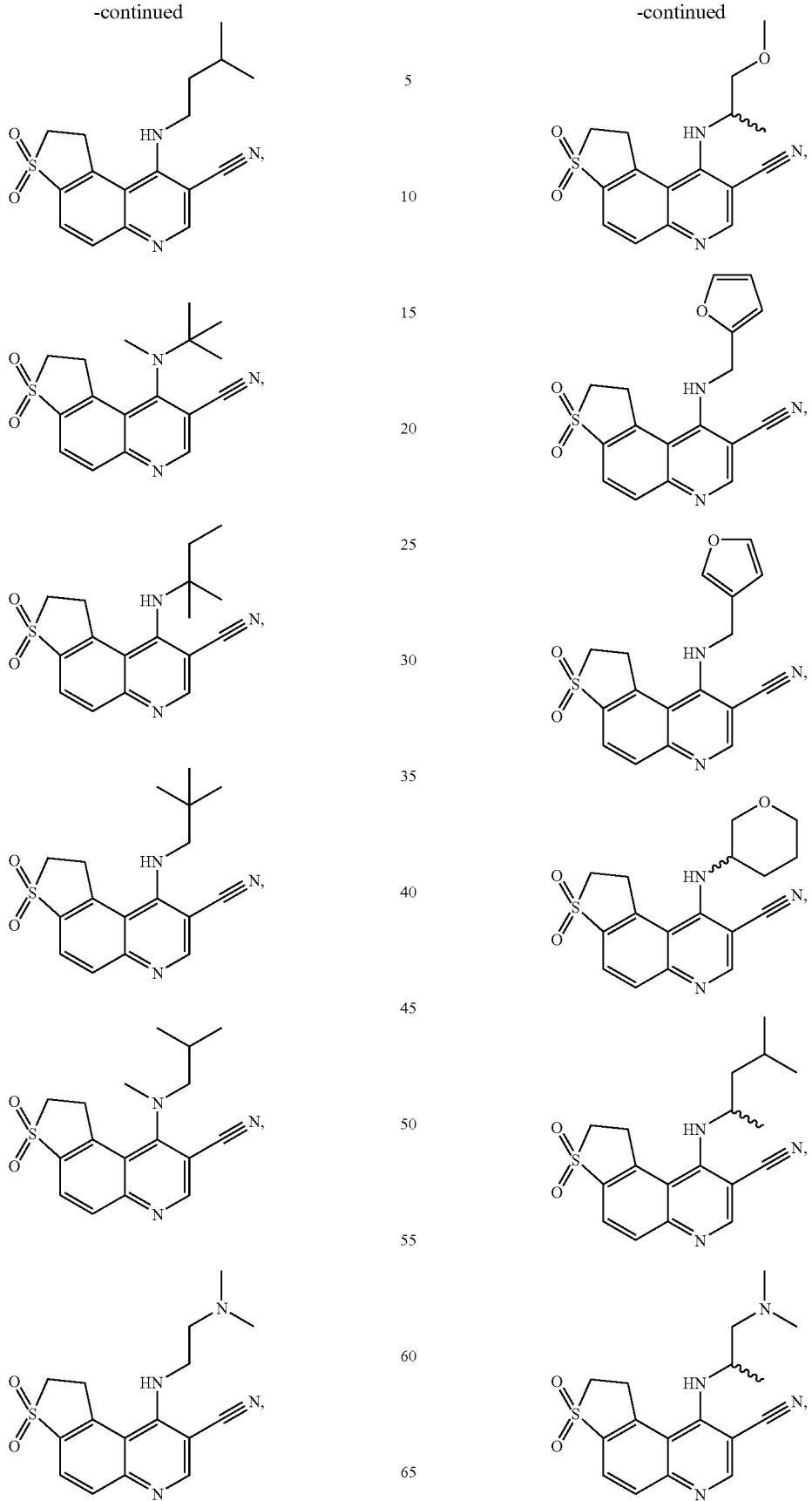

-continued
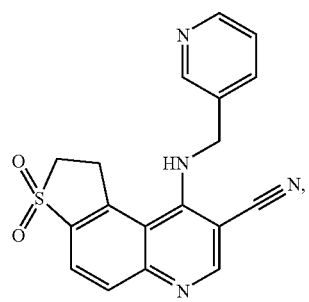
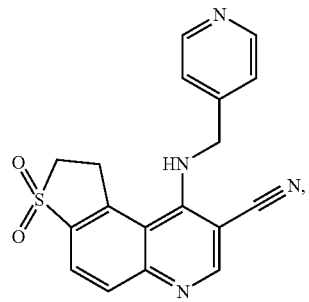
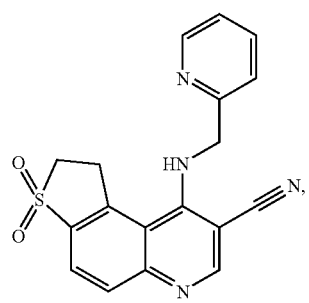
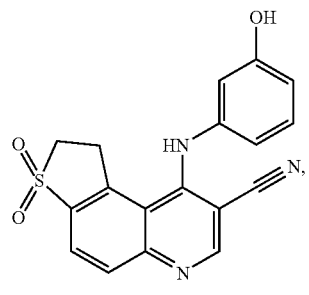
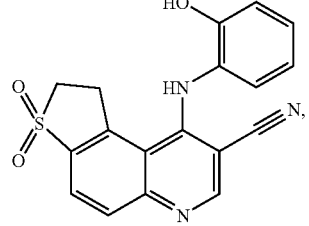
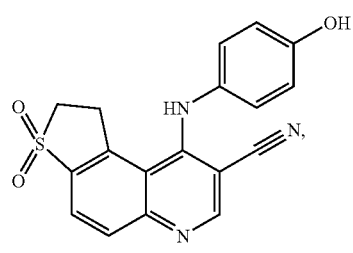
-continued
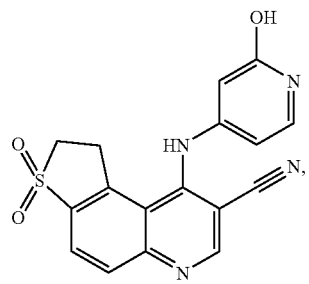
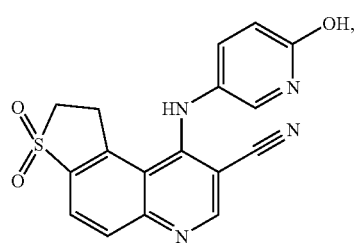
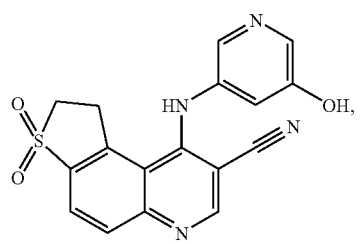
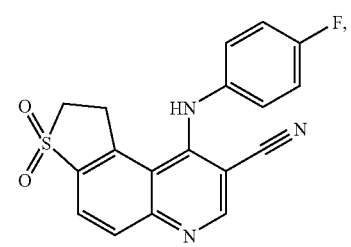
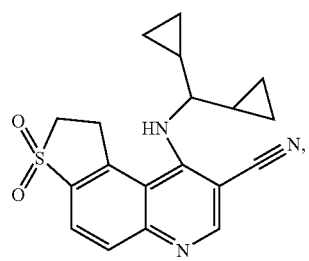
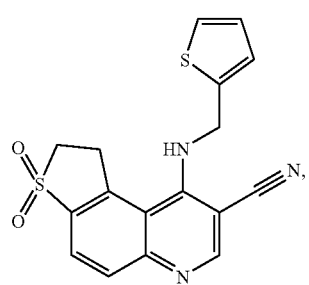

-continued
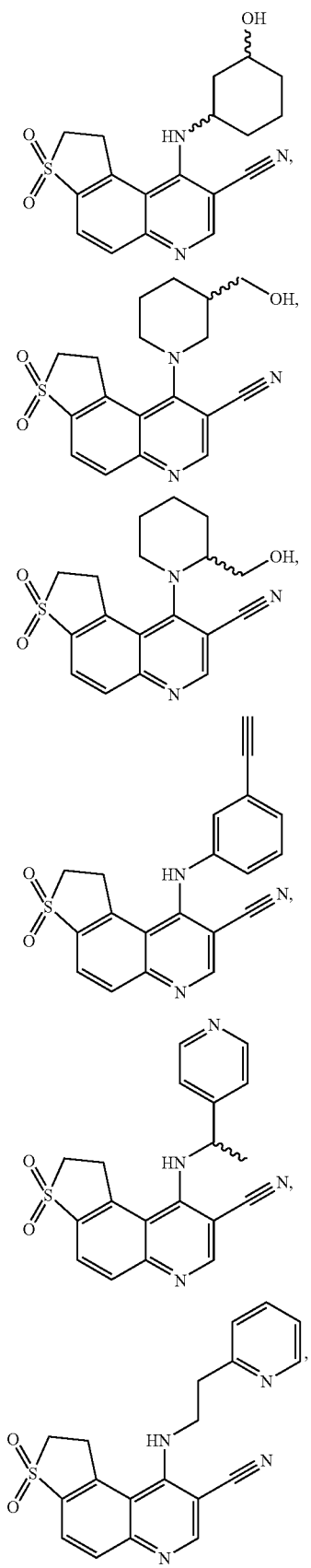
-continued
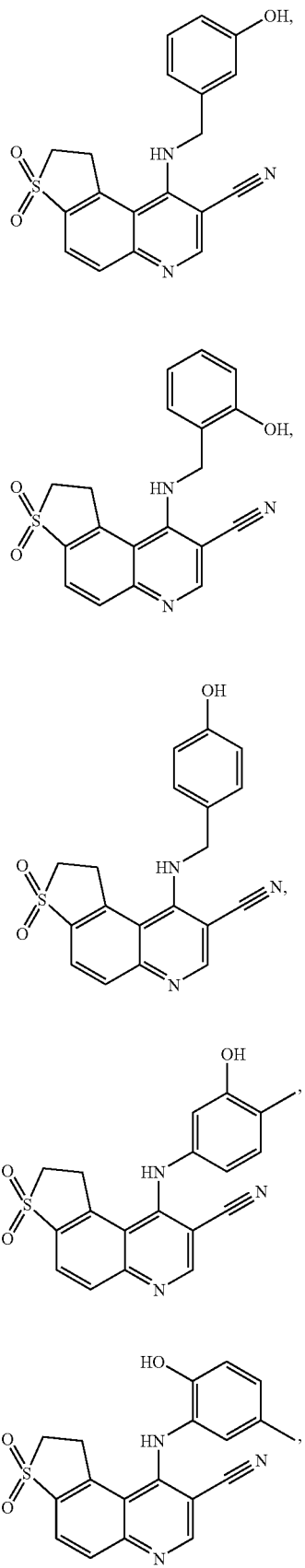

-continued
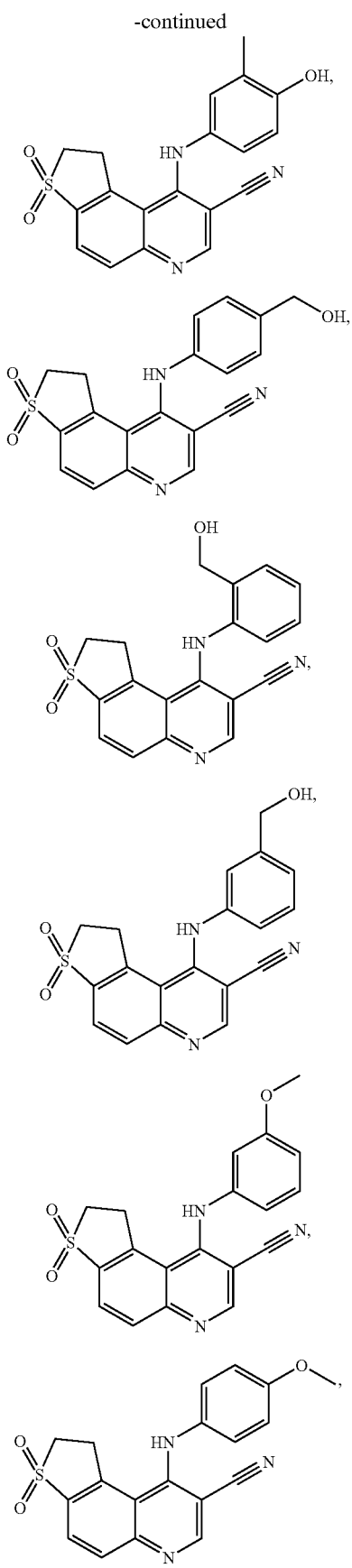
-continued
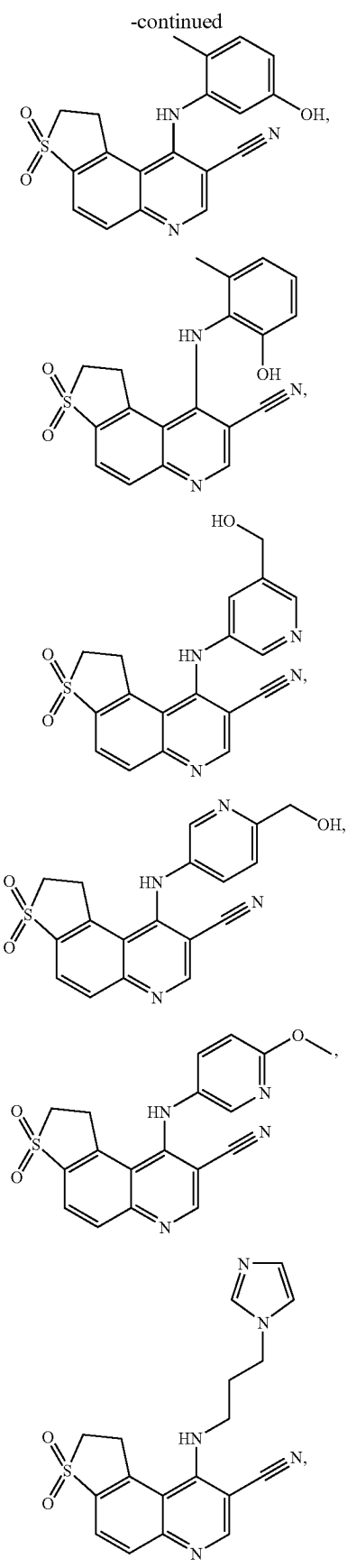

-continued
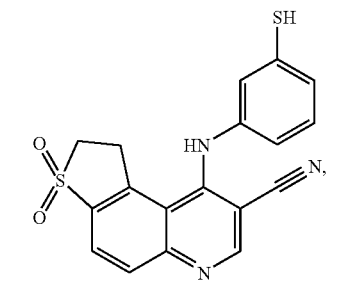
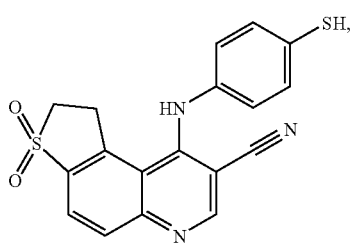
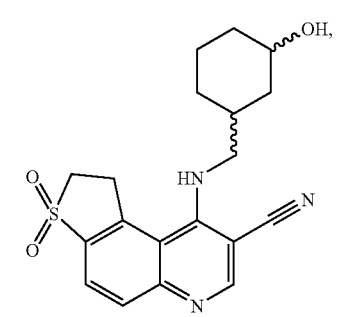
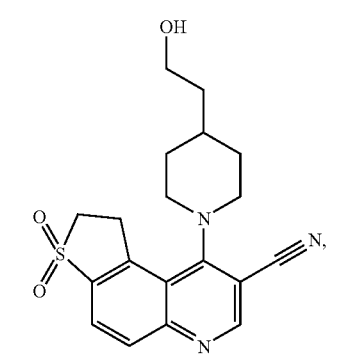
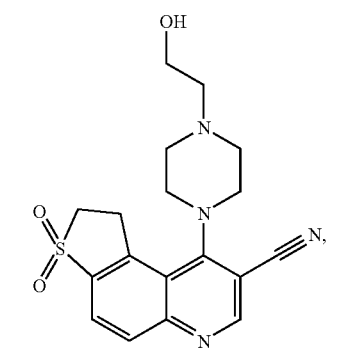
-continued
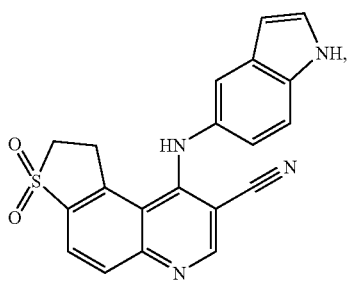
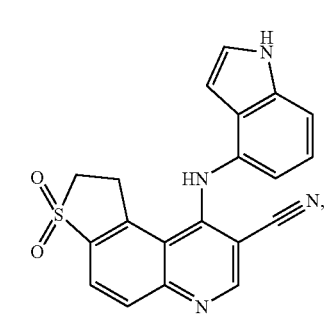
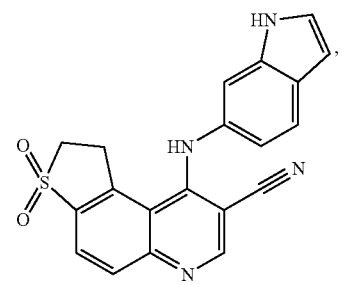
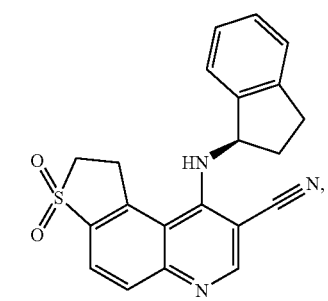
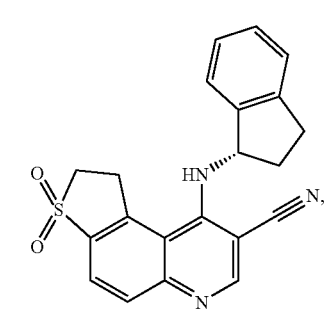

-continued
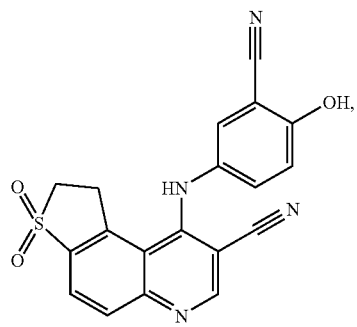
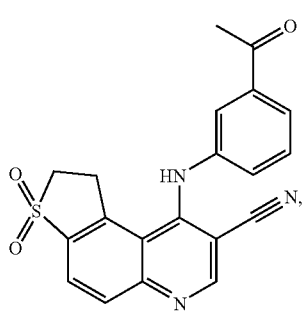
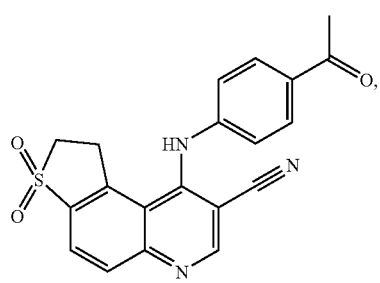
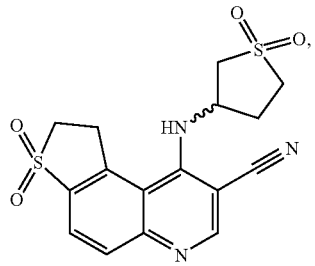
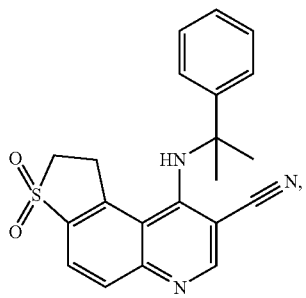
-continued
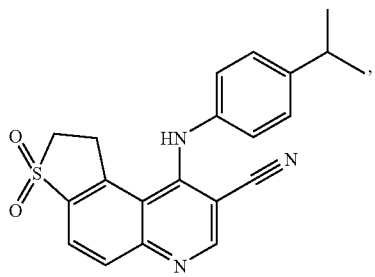
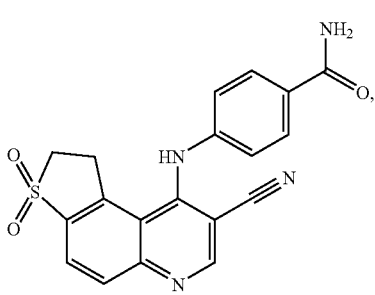
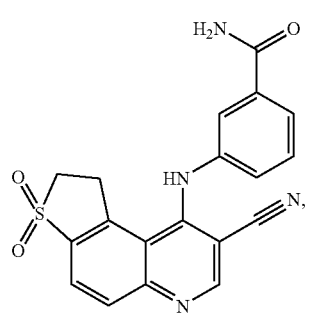
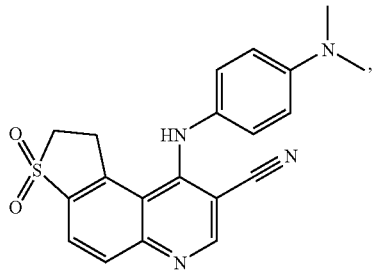
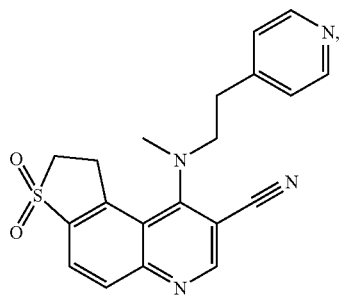

-continued
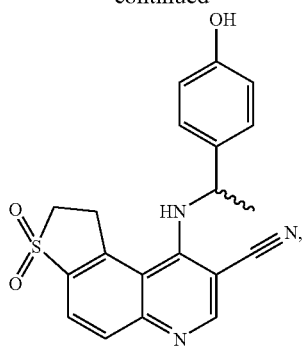
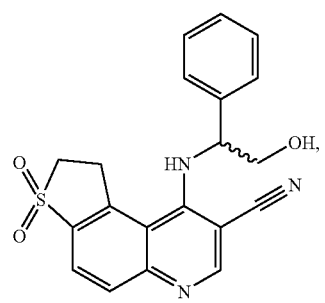
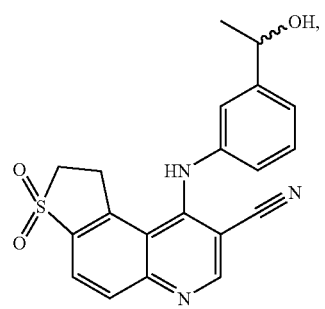
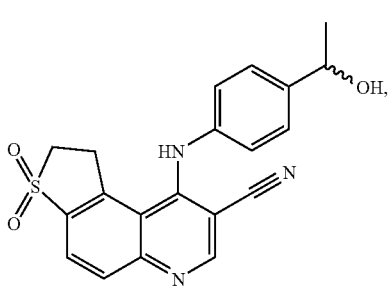
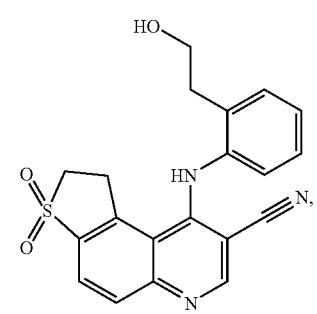
-continued
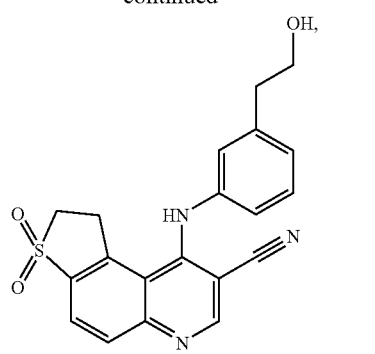
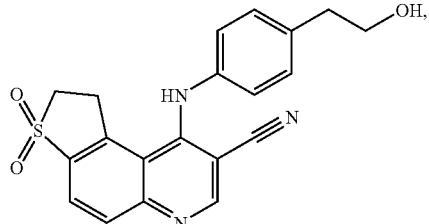
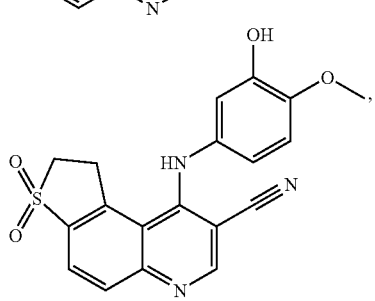
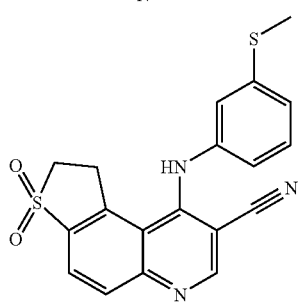
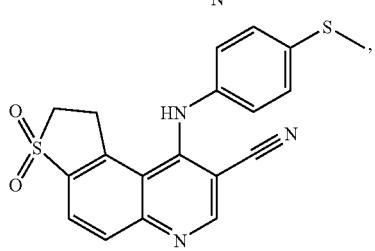
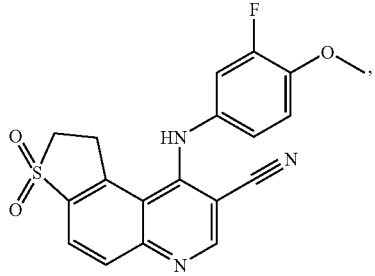

-continued
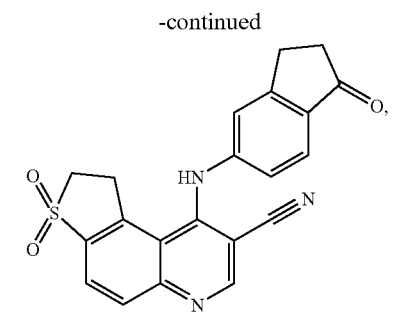
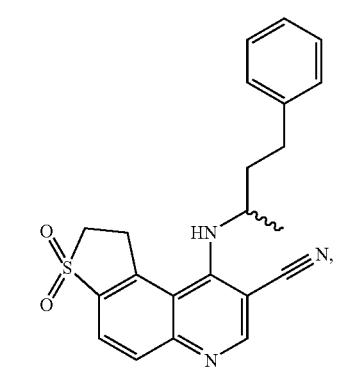
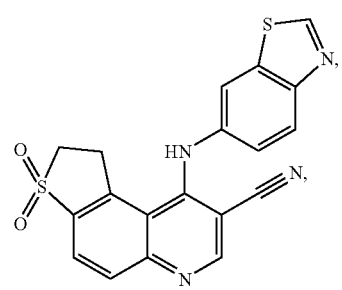
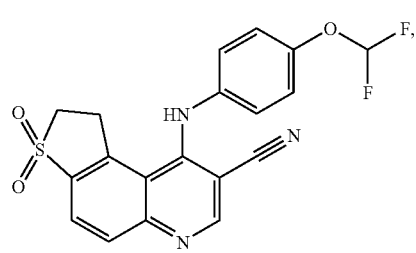
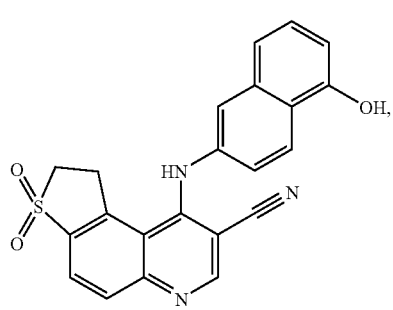
-continued
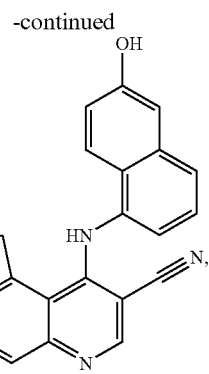
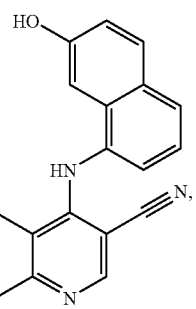
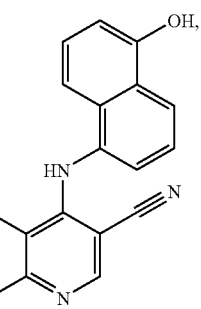
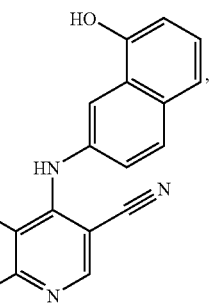
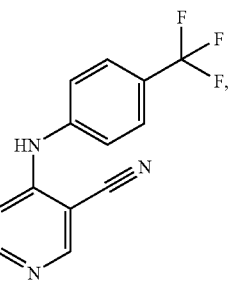

-continued

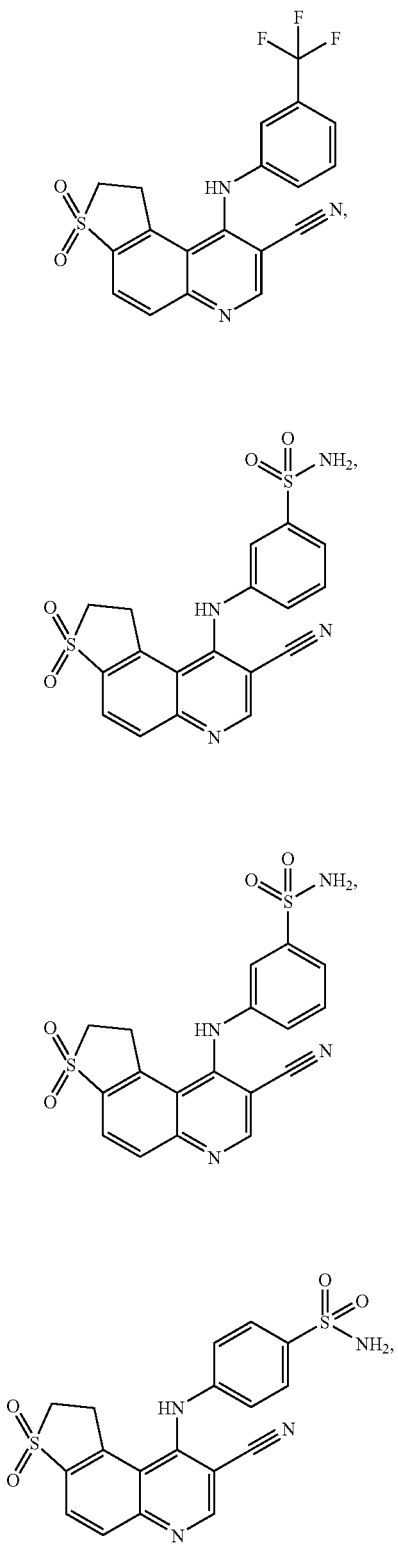

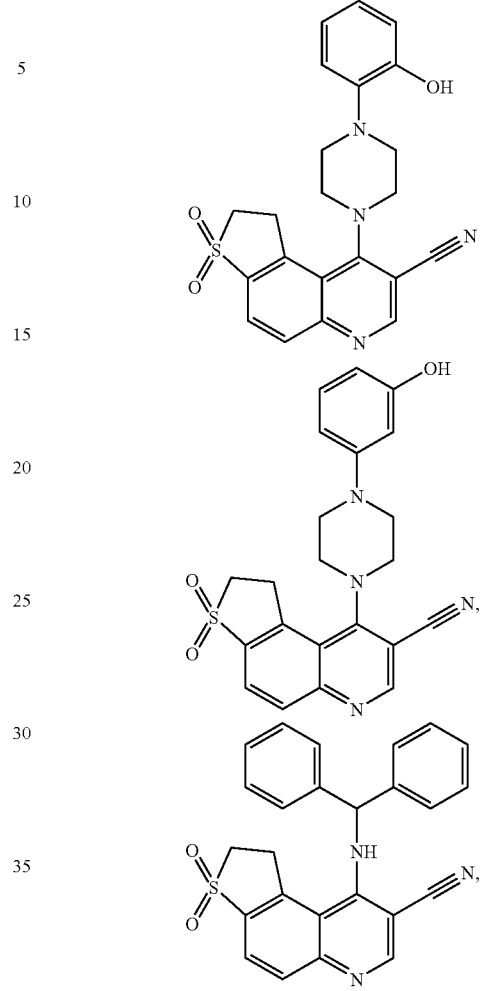

and physiologically tolerated salts thereof.

15. A compound according to claim 1, wherein —X—Y—Z— is —S(O)$_2$—CH$_2$—CH$_2$—.

16. A compound according to claim 1, wherein R$^2$ is H and R$^1$ is —C$_1$-C$_6$-alkyl which is unsubstituted or substituted one or more times by hydroxy, halogen, nitro, cyano, —NR$^5$R$^6$, —C(O)NR$^5$R$^6$, —S(O)$_2$NR$^5$R$^6$, —NR$^5$S(O)$_2$R$^6$, —NR$^5$C(O)R$^6$, —SR$^5$, —R$^5$ or —OR$^5$, and where the carbon framework the —C$_1$-C$_{10}$-alkyl optionally includes one or more nitrogen atoms, oxygen atoms, sulphur atoms, —NR$^4$ groups or C=O groups or one or more double bonds.

17. A compound according to claim 15, wherein R$^2$ is H and R$^1$ is —C$_1$-C$_6$-alkyl which is unsubstituted or substituted one or more times by hydroxy, halogen, nitro, cyano, —NR$^5$R$^6$, —C(O)NR$^5$R$^6$, —S(O)$_2$NR$^5$R$^6$, —NR$^5$S(O)$_2$R$^6$, —NR$^5$C(O)R$^6$, —SR$^5$, —R$^5$ or —OR$^5$, and where the carbon framework the —C$_1$-C$_{10}$-alkyl optionally includes one or more nitrogen atoms, oxygen atoms, sulphur atoms, —NR$^4$ groups or C=O groups or one or more double bonds.

* * * * *